US009524373B2

(12) United States Patent
Segal

(10) Patent No.: US 9,524,373 B2
(45) Date of Patent: Dec. 20, 2016

(54) GENOME-PHENOME ANALYZER AND METHODS OF USING SAME

(71) Applicant: SimulConsult, Inc., Chestnut Hill, MA (US)

(72) Inventor: Michael M. Segal, Chestnut Hill, MA (US)

(73) Assignee: SimulConsult, Inc., Chestnut Hill, MA (US)

(*) Notice: Subject to any disclaimer, the term of this patent is extended or adjusted under 35 U.S.C. 154(b) by 781 days.

(21) Appl. No.: 13/781,225

(22) Filed: Feb. 28, 2013

(65) Prior Publication Data

US 2013/0231404 A1 Sep. 5, 2013

Related U.S. Application Data

(60) Provisional application No. 61/605,724, filed on Mar. 1, 2012, provisional application No. 61/616,693, filed on Mar. 28, 2012, provisional application No. 61/719,579, filed on Oct. 29, 2012.

(51) Int. Cl.
*G01N 33/48* (2006.01)
*G06F 19/00* (2011.01)
*G06F 19/18* (2011.01)

(52) U.S. Cl.
CPC ......... *G06F 19/3437* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 4,667,292 A | 5/1987 | Mohlenbrock et al. | |
| 4,872,122 A | 10/1989 | Altschuler et al. | |
| 5,594,638 A | 1/1997 | Iliff | |
| 5,615,112 A | 3/1997 | Liu Sheng et al. | |
| 5,752,976 A | 5/1998 | Duffin et al. | |
| 5,902,234 A | 5/1999 | Webb | |
| 6,026,363 A | 2/2000 | Shepard | |
| 6,033,365 A | 3/2000 | von Zitzewitz | |
| 6,117,073 A | 9/2000 | Jones et al. | |
| 6,212,519 B1 | 4/2001 | Segal | |
| 6,539,101 B1 | 3/2003 | Black | |
| 6,579,231 B1 | 6/2003 | Phipps | |
| 6,754,655 B1 | 6/2004 | Segal | |
| 7,742,932 B2 | 6/2010 | Segal | |
| 2001/0056358 A1 | 12/2001 | Dulong et al. | |
| 2002/0019584 A1 | 2/2002 | Schulze et al. | |
| 2002/0087359 A1 | 7/2002 | Bocionek | |
| 2002/0128860 A1 | 9/2002 | Leveque et al. | |
| 2003/0125609 A1 | 7/2003 | Becker | |
| 2003/0191665 A1 | 10/2003 | Fitzgerald et al. | |

FOREIGN PATENT DOCUMENTS

EP 0457000 A2 11/1991

OTHER PUBLICATIONS

"2013 Best Practices Awards Winners Named—Bio-IT World," <http://www.bio-itworld.com/2013/4/10/best-practices-winners.html>, retrieved on Oct. 22, 2015 (2 pages).
DXplain, "DXplain Diagnostic Decision Support," <http://dxplain.org/dxp/dxp.pl>, retrieved on Jan. 14, 2010 (1 page).
Merriam-Webster Online Dictionary, "Fractionate," <www.merriam-webster.com/dictionary/fractionation>, retrieved on Jan. 20, 2010 (1 page).
"Fractionation," <http://medical-dictionary.thefreedictionary.com/p/fractionation>, retrieved on Jan. 20, 2010 (2 pages).
"Isabel Healthcare," <http://www.isabelhealthcare.com/home/default>, retrieved on Jan. 14, 2010 (1 page).
"OMIM Home," <http://www.ncbi.nlm.nih.gov/sites/entrez?db=omim>, retrieved on Jan. 14, 2010 (1 page).
"POSSUM Web," <http://www.possum.net.au>, retrieved on Jan. 14, 2010 (3 pages).
"SimulConsult," <http://www.simulconsult.com>, retrieved on Jan. 14, 2010 (1 page).
Allanson et al., "Elements of morphology: introduction," Am J Med Genet A. 149A(1):2-5 (2009).
Aronsky et al., "Evaluation of a computerized diagnostic decision support system for patients with pneumonia: study design considerations," J. Am. Med. Inform. Assoc. 8(5):473-85 (2001).
Avitzur, "How neurologists use the internet to enhance clinical decision-making," Neurology Today. 2(11):32-4 (2002).
Bankier et al., "POSSUM: the microcomputer laser-videodisk syndrome information system," Ophthalmic Paediartr. Genet. 10(1):51-2 (1989).
Barnett et al., "DXplain. An evolving diagnostic decision-support system," JAMA. 258(1):67-74 (1987).
Bates et al., "Ten commandments for effective clinical decisions support: making the practice of evidence-based medicine a reality," J. Am. Med. Inform. Assoc. 10(6):523-30 (2003).
Berner et al., "Effects of a decision support system on physicians' diagnostic performance," J. Am. Med. Inform. Assoc. 6(5):420-7 (1999).
Berner et al., "Performance of four computer-based diagnostic systems," N. Engl. J. Med. 330(25):1792-6 (1994).
Berner et al., "Relationships among performance scores of four diagnostic decision support systems," J. Am. Med. Inform. Assoc. 3(3):208-15 (1996).
Berner, "Diagnostic decisions support systems: how to determine the gold standard?" J. Am. Med. Inform. Assoc. 10(6):608-10 (2003).
Brownstein et al., "An international effort towards developing standards for best practices in analysis, interpretation and reporting of clinical genome sequencing results in the CLARITY Challenge," Genome Biol. 15(3):R53 (2014) (18 pages).
Budde et al., "tRNA splicing endonuclease mutations cause pontocerebellar hypoplasia," Nat Genet. 40(9):1113-8 (2008).

(Continued)

*Primary Examiner* — Jerry Lin
(74) *Attorney, Agent, or Firm* — Clark & Elbing LLP

(57) ABSTRACT

The present invention features methods, devices, and systems, e.g., for providing diagnostic or treatment decision support to a clinician for the diagnosis or treatment of a patient in need thereof or for diagnosing or treating a patient in need thereof.

34 Claims, 12 Drawing Sheets

(56) References Cited

OTHER PUBLICATIONS

Davies, "A Grand Vision for Genomic Medicine," <http://www.bio-itworld.com/2010/issues/sept-oct/first-base.html>, retrieved on Oct. 23, 2015 (2 pages).
de Dombal et al., "Computer-aided diagnosis of acute abdominal pain," Br. Med. J. 2(5804):9-13 (1972).
Dilber et al., "Pontocerebellar hypoplasia in two siblings with dysmorphic features," J Child Neurol. 17(1):64-6 (2002).
Dixon-Salazar et al., "Exome sequencing can improve diagnosis and alter patient management," Sci Transl Med. 4(138):138ra78 (2012) (13 pages).
Elstein et al., "Clinical problem solving and diagnostic decision making: selective review of the cognitive literature," BMJ 324(7339):729-32 (2002).
Elstein et al., "Effects of a decision support system on the diagnostic accuracy of users: a preliminary report," J. Am. Med. Inform. Assoc. 3(6):422-8 (1996).
Friedman et al., "Enhancement of clinicians' diagnostic reasoning by computer-based consultation: a multisite study of 2 systems," JAMA. 282(19):1851-6 Correction included (1999).
Gammon, "Watson Goes to the Hospital: Can IBM's Jeopardy winner help doctors treat their patients?" <http://www.technologyreview.com/news/423092/watson-goes-to-the-hospital>, retrieved Oct. 26, 2015 (3 pages) (2011).
Gorry et al., "Experience with a model of sequential diagnosis," Comput. Biomed. Res. 1(5):490-507 (1968).
Gorry, "Strategies for computer-aided diagnosis," Math. Biosci. 2(3):293-318 (1968).
Graber et al., "Diagnostic error in internal medicine," Arch Intern Med. 165(13):1493-9 (2005).
Guest et al., "The Online London Dysmorphology Database," Genet. Med. 1(5):207-12 (1999).
Hamosh et al., "Online Mendelian Inheritance in Man (OMIM), a knowledgebase of human genes and genetic disorders," Nucleic Acids Res. 30(1): 52-5 (2002).
Honeycutt et al., "Economic Costs Associated with Mental Retardation, Cerebral Palsy, Hearing Loss, and Vision Impairment—United States, 2003," <http://www.cdc.gov/mmwr/preview/mmwrhtml/mm5303a4.htm>, retrieved on Oct. 23, 2015 (5 pages).
Horrocks et al., "Computer-aided diagnosis: description of an adaptable system, and operational exerpience with 2,034 cases," Br. Med. J. 2(5804):5-9 (1972).
Johnson et al., "Medical informatics and pediatrics. Decision-support systems," Arch. Pediatr. Adolesc. Med. 149(12):1371-80 (1995).
Kassirer, "A report card on computer-assisted diagnosis—the grade: C," N. Engl. J. Med. 330(25):1824-5 (1994).
Kingsmore et al., "Deep sequencing of patient genomes for disease diagnosis: when will it become routine," Sci Transl Med. 3(87):87ps23 (2011) (4 pages).
Kong et al., "How medical professionals evaluate expressions of probability," N. Engl. J. Med. 315(12):740-4 (1986).
Maschke et al., "Clinical feature profile of spinocerebellar ataxia type 1-8 predicts genetically defined subtypes," Mov. Disord. 20(11):1405-12 (2005).
McSherry, "Avoiding premature closure in sequential diagnosis," Artif Intell Med. 10(3):269-83 (1997).
Michelson et al., "Evidence report: genetic and metabolic testing on children with global developmental delay: report of the Quality Standards Subcommittee of the American Academy of Neurology and the Practice Committee of the Child Neurology Society," Neurology. 77(17):1629-35 (2011).
Miller et al., "Quick Medical Reference (QMR): an evolving, microcomputer-based diagnostic decision-support program for general internal medicine," Proc. Annu. Symp. Comput. Appl. Med. Care. 8:947-8 (1989).
Miller et al., Clinical Diagnostic Decision Support Systems—An Overview. Clinical Decision Support Systems. E.S. Berner, 3-34 (1999).
Miller, "Evaluating evaluations of medical diagnostic systems," J. Am. Med. Inform. Assoc. 3(6):429-31 (1996).
Miller, "Medical diagnostic decision support systems—past, present, and future: a threaded bibliography and brief commentary," J Am Med Inform Assoc. 1:8-27 (1994).
Newman-Toker et al., "Diagnostic errors—the next frontier for patient safety," JAMA. 301(10):1060-2 (2009).
Norman et al., "Iterative diagnosis," BMJ 339:b3490 (2009) (5 pages).
Osheroff et al., "A roadmap for national action on clinical decision support," J. Am. Med. Inform. Assoc. 14(2):141-5 (2007).
Ramnarayan et al., "ISABEL: a web-based differential diagnostic aid for paediatrics: results from an initial performance evaluation," Arch. Dis. Child. 88(5): 408-13 (2003).
Ramnarayan et al., "Measuring the impact of diagnostic decision support on the quality of clinical decision making: development of a reliable and valid composite score," J. Am. Med. Inform. Assoc. 10(6):563-72 (2003).
Schattner et al., "The hazards of diagnosis," QJM. 103(8):583-7 (2010) (5 pages).
Schiff et al. "Diagnostic error in medicine: analysis of 583 physician-reported errors," Arch Intern Med. 169(20):1881-7 (2009).
Schwartz et al., "Artificial intelligence in medicine. Where do we stand?" N. Engl. J. Med. 316(11):685-8 (1987).
Schwartz, "Medicine and the computer: the promise and problems of change," N. Engl. J. Med. 283(23):1257-64 (1970).
Segal et al., "Clinical pertinence metric enables hypothesis-independent genome-phenome analysis for neurologic diagnosis," J. Child. Neurol. 30(7): 881-8 (2015).
Segal et al., "Health 2.0 for Neurologists," <http://patients.aan.com/news/?event=read&article_id=5277> retrieved on Oct. 26, 2015 (5 pages) (2008).
Segal, "Diagnostic software as a knowledge-accumulating system for understanding and preventing diagnositc errors," Diagnostic Errors in Medicine Annual Meeting, (2009) (9 pages) (Abstract Included).
Segal, "How doctors think, and how software can help avoid cognitive errors in diagnosis," Acta Paediatr. 96(12):1720-22 (2007).
Segal, "Medical Decision Support Software: Have Our Hopes and Fears Come True?" <http://www.hcplive.com/journals/mdng-neurology/2008/nov2008/medical_decision_support_software> retrieved on Oct. 26, 2015 (4 pages).
Segal, "Mobile medical computing driven by the complexity of neurologic diagnosis," J. Child. Neurol. 21(7):595-9 (2006).
Segal, "Neural network programs: explorations in parallel distributed processing," Science. 241(4869):1107-8 (1988).
Sim et al., "Clinical decision support systems for the practice of evidence-based medicine," J. Am. Med. Inform. Assoc. 8(6):527-34 (2001).
Singh et al., "Errors of diagnosis in pediatric practice: a multi-site survey," Pediatrics. 126(1):70-9 (2010) (17 pages).
Stevenson et al., "Health-related quality of life measures in genetic disorders: an outcome variable for consideration in clinical trials," Am J Genet C Semin Med Genet. 151C(3):255-60 (2009).
Szolovits et al., "Artificial intelligence in medical diagnosis," Ann. Intern. Med. 108(1):80-7 (1988).
Szolovits et al., "Categorical and probabilistic reasoning in medical diagnosis," Artif Intell. 11(1):115-44 (1978).
Tamarin, Chapter 5: Pedigree Analysis. *Principles of Genetics, Fourth Edition*. 82-85, 1993.
Tang et al., "Googling for a diagnosis—use of Google as a diagnostic aid: internet based study," BMJ. 333(7579):1143-5 (2006).
Teach et al., "An analysis of physician attitudes regarding computer-based clinical consultation systems," Comput Biomed Res. 14(6):542-58 (1981).
Tu et al., "Episodic skeletal-plan refinement based on temporal data," Commun ACM. 32(12):1439-55 (1989).
Waxman et al., "Computer-assisted adult medical diagnosis: subject review and evaluation of a new microcomputer-based system," Medicine (Baltimore). 69(3):125-36 (1990).

(56) References Cited

OTHER PUBLICATIONS

Wright et al., "Clinical decision support capabilities of commercially-available clinical information systems," J. Am. Med. Inform. Assoc. 16(5):637-44 (2009).
Campuzano et al., "Determining the pathogenicity of genetic variants associated with cardiac channelopathies," Sci Rep. 5:7953 (2015) (6 pages).
González-Pérez et al., "Improving the assessment of the outcome of nonsynonymous SNVs with a consensus deleteriousness score, condel," Am J Hum Genet. 88(4):440-9 (2011).
Hu et al., "VAAST 2.0: improved variant classification and disease-gene identification using a conservation-controlled amino acid substitution matrix," Genet Epidermiol. 37(6):622-34 (2013).
Li et al., "A comprehensive framework for prioritizing variants in exome sequencing studies of Mendelian diseases," Nucleic Acids Res. 40(7):e53 (2012) (8 pages).
Li et al., "Automated inference of molecular mechanisms of disease from amino acid substitutions," Bioinformatics. 25(21):2744-50 (2009).
Tabor et al., "Pathogenic variants for mendelian and complex traits in exomes of 6,517 European and African Americans: implications for the return of incidental results," Am J Hum Genet. 95(2):183-93 (2014).
Yandell et al., "A probabilistic disease-gene finder for personal genomes," Genome Res. 21(9):1529-42 (2011).

| Variant table | | | | Comments | |
|---|---|---|---|---|---|
| HGNC symbol | Proband % | Mono Severity | Biallelic Severity | Inheritance | Interpretation |
| SCN1A | 50 | 1 | 1 | AD | SCN1A (monoallelic) severity 1 |
| SCN1A | 50 | 3 | 3 | AD | SCN1A (monoallelic) severity 3 |
| SCN1A | 50 | 2 | 2 | AD | SCN1A (monoallelic) severity 3 |
| VLDLR | 100 | 4 | 4 | AR | VLDLR (biallelic) severity 4 |
| CTDP1 | 50 | 4 | 4 | AR | Not used since 50% not disease-causing |
| ATP7B | 50 | 3 | 3 | AD/AR | ATP7B (monoallelic) severity 3 |
| VPS13B | 50 | 2 | 2 | AR | Not used since 50% not disease-causing |
| VPS13B | 50 | 4 | 4 | AR | VPS13B (biallelic) severity 2 compound heterozygote |
| VPS13B | 50 | 2 | 3 | AR | Severity now 3 since worst are 4 and 3 severity |
| ARX | 50 | 3 | 3 | XR | ARX (X-linked) severity 3 |
| OTC | 50 | 4 | 4 | XR | OTC (X-linked) severity 4 |
| MT-ATP6 | 100 | 1 | 1 | M | MT-ATP6 (mitochondrial) severity 1 |
| POTEF | 50 | 3 | 3 | | Not recognized (reported as not imported) |

| Differential diagnosis | Add findings | Add tests | Patient | ☐ Advanced mode |
|---|---|---|---|---|
| | | | | To home screen |

Diseases
- Cohen syndrome
- Dravet syndrome
- Wilson disease hetero
- Febrile seizures
- Noonan syndrome
- CMV infection, sympt
- CHARGE syndrome
- Fetal alcohol syndron
- Rubella, congenital
- Cerebral palsy, sever
- OTC, female heteroz
- Chromosome 5p dele
- Smith-Lemli-Opitz sy
- Williams syndrome
- Phelan-McDermid sy
- Citrin deficiency: NIC
- PMM2-CDG (CDG-I
- Chromosome 18p del
- OTC, early onset mal
- Costello syndrome (f
- Smith-Magenis syndr
- ARX mental retardati
- VLDLR associated c 12 month old girl:   Change initial information   Show patient summary   Color key Pertinence

Pertinent positive findings

| | | |
|---|---|---|
| 3c | ✓ | VPS13B (COH1) gene mutations (biallelic) |
| | @1w | Hypotonia |
| | @1w | Weight low (< 3rd %ile) |
| 3 | ✓ | SCN1A gene mutation (monoallelic) |
| 3 | ✓ | ATP7B gene mutation (monoallelic) |
| 4 | ✓ | OTC gene mutation (X-linked) |
| 3 | ✓ | ARX gene mutation (X-linked) |
| 4 | ✓ | VLDLR gene mutations (biallelic) |
| 1 | ✓ | MT-ATP6 gene mutations (mitochondrial) |

Pertinent negative findings

| | | |
|---|---|---|
| x | | Early death if undiagnosed |

Tip: Orphanet: Cohen syndrome   More tips
Tip: GeneReviews: Cohen syndrome   OMIM

| Gene discovery: unrecognized genes & zygosity after novelty / compound heterozygote analysis |||
| --- | --- | --- |
| Unrecognized: <br> • Human phenotypes <br> • Monoallelic phenotypes <br> • Biallelic phenotypes | Sort by: <br> • Severity <br> • Alphabetical <br> • Order read | Display: <br> • Buttons <br> • Tab-separated for spreadsheet |

| | | | |
| --- | --- | --- | --- |
| • AP2M1 monoallelic 4 | AP2M1 biallelic 0 | HGNC | HGMD |
| ARMCX2 X-linked 4 | X-linked 0 | HGNC | HGMD |
| ARMCX3 X-linked 4 | X-linked 0 | HGNC | HGMD |
| ARMCX6 X-linked 4 | X-linked 0 | HGNC | HGMD |
| ATP6AP1 X-linked 4 | X-linked 0 | HGNC | HGMD |
| BDKRB2 monoallelic 4 | BDKRB2 biallelic 0 | HGNC | HGMD |
| • BGN X-linked 4 | X-linked 0 | HGNC | HGMD |

Gene variants: Click a gene to see variants

Set variant parameters | Copy text | Finish

Fig. 7

| Differential diagnosis | Add findings | Add tests | Patient | | Advanced mode / To home screen |

Diseases
- Dravet syndrome
- Cohen syndrome
- Febrile seizures
- VLDLR-associated ce
- Wilson disease hetero
- West syndrome (infan
- ARX mental retardati
- GEFS+1: Generalize
- MAE: Doose myoclon
- Proud agenesis of the
- Epilepsy, idiopathic
- Rasmussen subacute
- EIEE1: epileptic ence
- OTC, early onset mal
- LISX2: Lissencephaly
- Dengue encephalitis
- Cerebral malaria
- OTC, female heterozy
- CP: cerebral palsy, m
- Cerebral palsy, sever
- Agenesis of the corpu

12 month old girl:  Change initial information | Show patient summary | Color key: Pertinence

Pertinent positive findings

|   | ≤ 3m | Seizures |
|---|------|----------|
| 3 | ✓ | SCN1A gene mutation (monoallelic) |
| 3c | ✓ | VPS13B (COH1) gene mutations (biallelic) |
| 4 | ✓ | VLDLR gene mutations (biallelic) |
| 3 | ✓ | ATP7B gene mutation (monoallelic) |
| 3 | ✓ | ARX gene mutation (X linked) |
| 4 | ✓ | OTC gene mutation (X-linked) |
| 1 | ✓ | MT-ATP6 gene mutations (mitochondrial) |

Pertinent negative findings

| | | |
|---|---|---|
| X | | +Heat or fever triggers attacks or aggravates findings |
| X | | Early death if undiagnosed |

More tips

Tip: GeneReviews: SCN1A-Related Seizure Disorders     OMIM

Fig. 8

| Differential diagnosis | Add findings | Add tests | Patient | | Advanced mode / To home screen |
|---|---|---|---|---|---|

Diseases

- Cohen syndrome
- VLDLR-associated ce
- Wilson disease hetero
- Dravet syndrome
- ARX mental retardati
- Proud agenesis of the
- Febrile seizures
- Epilepsy, idiopathic
- EIEE1: epileptic ence
- OTC, early onset mal
- West syndrome (infan
- LISX2: Lissencephaly
- Dengue encephalitis
- Cerebral malaria
- OTC, female heterozy
- CP: cerebral palsy, m
- GEFS+1: Generalized
- Cerebral palsy, severe
- Agenesis of the corpu
- Leigh-like syndrome
- Toxoplasmosis, sympt 12 month old girl: | Change initial information | Show patient summary | Color key: Pertinence |

Pertinent positive findings

| | ≤3m | Seizures |
|---|---|---|
| 1 | √ | SCN1A gene mutation (monoallelic) |
| 3c | √ | VPS13B (COH1) gene mutations (biallelic) |
| 4 | √ | VLDLR gene mutations (biallelic) |
| 3 | √ | ATP7B gene mutation (monoallelic) |
| 3 | √ | ARX gene mutation (X-linked) |
| 4 | √ | OTC gene mutation (X-linked) |
| 1 | √ | MT-ATP6 gene mutations (mitochondrial) |

Pertinent negative findings

| x | +Heat or fever triggers attacks or aggravates findings |
|---|---|
| x | Early death if undiagnosed |

Tip: NINDS Hypotonia Information Page    More tips

Tip: NeuroExam article on testing tone    OMIM

| Variant table | | | | | | Comments | |
|---|---|---|---|---|---|---|---|
| HGNC symbol | Proband % | Mother % | Father % | Mono Severity | Biallelic Severity | Inherit | Interpretation |
| SCN1A | 50 | 50 | 0 | 1 | 1 | AD | Not novel for monoallelic since present in mother |
| SCN1A | 50 | 0 | 0 | 3 | 3 | AD | SCN1A (monoallelic) severity 3 |
| SCN1A | 50 | 0 | 0 | 2 | 2 | AD | SCN1A (monoallelic) severity 3 |
| VLDLR | 100 | 50 | 50 | 4 | 4 | AR | VLDLR (biallelic) severity 4 |
| CTDP1 | 50 | 0 | 0 | 4 | 4 | AR | Not imported even though novel since not disease-causing |
| ATP7B | 50 | 0 | 0 | 3 | 3 | AD/AR | ATP7B (monoallelic) severity 3 |
| VPS13B | 50 | 50 | 0 | 2 | 3 | AR | Not registered since only monoallelic |
| VPS13B | 50 | 50 | 0 | 4 | 4 | AR | Still not registered since both variants are maternal |
| VPS13B | 50 | 0 | 50 | 2 | 2 | AR | VPS13B (biallelic) severity 2 compound heterozygote |
| VPS13B | 50 | 0 | 0 | 2 | 3 | AR | Severity now 3 since maternal 4 and novel 3 biallelic severity |
| ARX | 50 | 0 | 0 | 3 | 3 | XR | ARX (X-linked) monoallelic severity 3 |
| OTC | 50 | 0 | 0 | 4 | 4 | XR | OTC (X-linked) monoallelic severity 4 |
| MT-ATP6 | 100 | 0 | 0 | 1 | 1 | M | MT-ATP6 (mitochondrial) severity 1 |

GENOME-PHENOME ANALYZER AND METHODS OF USING SAME

CROSS-REFERENCE TO RELATED APPLICATIONS

This application claims benefit of priority to U.S. Provisional Application No. 61/605,724, filed Mar. 1, 2012, U.S. Provisional Application No. 61/616,693, filed Mar. 28, 2012, and U.S. Provisional Application No. 61/719,579, filed Oct. 29, 2012, each of which is hereby incorporated by reference in its entirety.

STATEMENT REGARDING FEDERALLY SPONSORED RESEARCH

This invention was made with government support under grant number 5R42HG006974 from the National Human Genome Research Institute. The government has certain rights to the invention.

BACKGROUND OF THE INVENTION

The cost of sequencing the entire human genome has fallen low enough that the main concerns about the clinical usefulness of whole genome information are now about the difficulty of interpreting the mass of information. Existing methods, e.g., involving whole-exome or whole-genome sequencing, report genome information as raw lists of genes or other chromosomal regions found to be abnormal and report the diseases associated with abnormalities in a large number of genes. However, current approaches to utilizing such raw genomic data are of limited utility to a clinician seeking to make a diagnosis. There is a pressing need in the art to develop an accurate, efficient, and quantitative computer-based diagnostic decision support tool that receives genome data from a patient and uses these data to compute the probability of various diseases and the pertinence of various gene variants, thereby providing diagnostic decision support to the clinician.

SUMMARY OF THE INVENTION

In general, the invention features methods, devices, and systems for providing diagnostic or treatment decision support to a clinician for the diagnosis or treatment of a patient in need thereof, for assisting in the diagnosis or treatment of a patient in need thereof, or for diagnosing or treating a patient in need thereof.

The invention features a method, e.g., a method of providing decision support to a clinician for the diagnosis or treatment of a patient in need thereof, or a method of assisting in the diagnosis or treatment of a patient in need thereof, including the steps of: (a) providing, in a physical computing device, a representation of a set of candidate diseases and associated initial parameters representing estimated probabilities of the candidate diseases; (b) receiving, in the computing device, a plurality of patient findings for the patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations, for one or more parents, siblings, or other family members; (c) using the computing device to iteratively modify the initial parameters representing estimated probabilities of the candidate diseases using each of the plurality of patient findings, thereby obtaining modified parameters representing modified estimated probabilities of the candidate diseases; and (d) outputting a candidate disease list capable of being displayed, the candidate disease list including one or more of the candidate diseases having highest modified estimated probabilities.

In some embodiments, step (c) of the method includes using a Bayesian method to obtain the modified parameters representing modified estimated probabilities of the candidate diseases.

In some embodiments, the method further includes: in step (a), providing, in the computing device, a first set of quantities representing estimated probabilities of a plurality of patient findings in the general non-diseased population, and a second set of quantities representing estimated probabilities of a plurality of patient findings each assuming the presence of a specified candidate disease; and in step (c), using the first set of quantities and second set of quantities of step (a) to iteratively modify the initial parameters representing estimated probabilities of the candidate diseases using each of the plurality of patient findings, thereby obtaining the modified parameters representing the modified estimated probabilities of the candidate diseases. For example, the one or more severity scores for each genetic variant identified may be used to modify one of the first set of quantities, the one of the first set of quantities representing an estimated probability of an abnormal gene with the genetic variant in the general non-diseased population. In particular, in some embodiments, a higher severity score for the genetic variant results in a lower one of the first set of quantities representing an estimated probability of the abnormal gene with the genetic variant in the general non-diseased population.

In some embodiments, the genetic sequencing information associated with the patient includes identification of a plurality of genetic variants each associated with the same gene, and the genetic variant having the highest severity score among the genetic variants each associated with the gene is used to modify one of the first set of quantities representing the estimated probability of the abnormal gene corresponding to the genetic variant absent information about the presence of a specified candidate disease.

In some embodiments, the severity score corresponding to each genetic variant is calculated by the computing device as a quantitative result from a plurality of inputs. The plurality of inputs may include, e.g., variant information from one or more other individuals, e.g., parents, siblings, or other family members of the patient. In some embodiments, the plurality of inputs includes an input selected from the group consisting of: zygosity in one or more other family members sequenced, frequency of the genetic variant in the general population, chromosome location, type of the genetic variant, functional score, conservation score, splice prediction score, depth of read score, read quality score, and score based on whether the genetic variant is known to cause disease. In some embodiments, the plurality of inputs includes a pathogenicity model selected from the group consisting of a loss of function pathogenicity model and a gain of function pathogenicity model.

In some embodiments, the patient findings include, for at least one of the genetic variants identified, or for each of the genetic variants identified, both a monoallelic severity score and a biallelic severity score. For example, the monoallelic severity score may be used when the corresponding genetic variant is considered to cause a monoallelic disease, and the biallelic severity score may be used when the corresponding genetic variant is considered to cause a biallelic disease. In some embodiments, the monoallelic severity score is reduced, relative to the biallelic severity score, when the frequency of the corresponding genetic variant exceeds a threshold percentage of the population, e.g., 0.005%, 0.01%, 0.02%, 0.05%, 0.1%, 0.2%, 0.5%, 1%, 2%, or 5%.

In some embodiments, the measure of zygosity for each genetic variant identified is a measure of the fraction of sequenced genetic material that includes the genetic variant. For example, the measure of zygosity for each genetic variant may be used to categorize the genetic variant as autosomal monoallelic, autosomal biallelic, X-linked monoallelic, X-linked biallelic, Y-linked, or mitochondrial. In addition, the genetic sequencing information associated with the patient may include identification of two genetic variants each associated with the same gene, the two genetic variants each having monoallelic zygosity and the gene being associated with a recessive disease, and wherein the two genetic variants are collectively categorized as possibly having compound heterozygosity. In some embodiments, the two genetic variants are collectively categorized as having a severity score corresponding to the lesser of the severity scores of the two genetic variants. In some embodiments, the genetic sequencing information associated with the patient includes identification of more than two genetic variants each associated with the same gene, the more than two genetic variants each having monoallelic zygosity and the gene being associated with a recessive disease, and wherein the more than two genetic variants are collectively categorized as possibly having compound heterozygosity and having a severity score corresponding to the lesser of the highest two severity scores of the more than two genetic variants.

In some embodiments, the genetic sequencing information associated with the patient includes identification of two genetic variants each associated with the same gene, the two genetic variants each having monoallelic zygosity and the gene being associated with a recessive disease, wherein genetic sequencing information further includes chromosomal location of the genetic variants, and wherein, if the chromosomal location is the same for each of the two genetic variants, the two genetic variants are not categorized as having compound heterozygosity.

In some embodiments, at least one of the genetic variants is of previously unidentified phenotype, wherein the genetic sequencing information includes chromosomal location for the genetic variant, and wherein the measure of zygosity and the chromosomal location for the genetic variant are used to categorize the genetic variant as autosomal monoallelic, autosomal biallelic, X-linked monoallelic, X-linked biallelic, Y-linked, or mitochondrial.

In some embodiments, the patient findings further include, for at least one of the genetic variants identified, or for each of the genetic variants identified, information about a parent, sibling, or other family member of the patient, e.g., the mother and/or father of the patient, the information including a measure of zygosity of the genetic variant in the family member, e.g., the mother and/or the father.

In some embodiments, the information about the parent, sibling, or other family member of the patient, e.g., the mother and/or father, is used to eliminate at least one compound heterozygote possibility, thereby resulting in a refined determination of the severity score. In some embodiments, at least one genetic variant determined to be monoallelic in the patient is eliminated based on the presence of the monoallelic genetic variant in the mother or father.

In some embodiments, both parents are unaffected; in other embodiments, one or both parents may be affected, and/or siblings or other family members, whether unaffected or affected, may also or alternatively be included in the analysis.

In some embodiments, the patient findings include identification of 2, 5, 10, 20, 50, 100, 200, 500, 1,000, 2,000, or more genetic variants.

In some embodiments, the patient findings further include information that is not obtained from genetic sequencing of genetic material from the patient. For example, the information that is not obtained from genetic sequencing of the genetic material from the patient may include, e.g., information about a symptom, sign, medical history, presence or absence of similar disease in one or more family members or others nearby, laboratory test result, clinical result, environmental factor, historical information, or demographic profile associated with the patient.

In some embodiments, step (c) further includes calculating the pertinence of one or more of the patient findings in light of other patient findings; and step (d) further includes outputting a patient finding list capable of being displayed, the patient finding list including one or more of the patient findings displayed with their pertinence in light of other patient findings. For example, calculating the pertinence of one or more of the patient findings may be performed in light of all other of the patient findings received in the computing device, and the patient finding list may include one or more of the patient findings displayed with their pertinence in light of all other of the patient findings received in the computing device. In some embodiments, the one or more of the patient findings is one or more genetic variants.

In some embodiments, step (d) includes transmitting the candidate disease list over the Internet or to a display device. For example, step (d) may further include outputting to the display device the modified estimated probabilities of the one or more candidate diseases having highest modified estimated probabilities in rank order. In particular, the method may further include performing steps (b)-(d) at least twice, wherein the second time step (b) is performed, a different plurality of patient findings is received by the computing device, resulting in outputting to the display device different of the modified estimated probabilities of the one or more candidate diseases having highest modified estimated probabilities in rank order. For example, the different plurality of patient findings may include a further patient finding, or the further patient finding may replace a previous patient finding.

In some embodiments, the method results in the diagnosis of the patient as having one of the candidate diseases having highest modified estimated probabilities.

In some embodiments, the method results in the identification of one or more genes as having highest pertinence. For example, this may result in the identification of one or more relationships between each gene and a corresponding known disease or new variant similar to the known disease. In some embodiments, the method results in the identification of two or more genes as having highest pertinence, wherein the identification of each of the two or more genes as having highest pertinence results in the identification of relationships between each gene and a corresponding known disease or new variant similar to the known disease, and wherein the method results in the diagnosis of the patient as having each the corresponding known disease or new variant similar to the known disease.

In some embodiments, the physical computing device is accessed and operated over the Internet.

In some embodiments, the associated initial parameters are estimated probabilities of the candidate diseases. For example, the modified parameters may be modified estimated probabilities of the candidate diseases.

The invention further features devices and systems for practicing the methods described herein. For example, the invention further features a computer readable medium having stored thereon executable instructions for directing a physical computing device to implement a method including the steps of: (a) providing, in the computing device, a representation of a set of candidate diseases and associated initial parameters representing estimated probabilities of the candidate diseases; (b) receiving, in the computing device, a plurality of patient findings for a patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations, for one or more parents, siblings, or other family members; (c) iteratively modifying the initial parameters representing estimated probabilities of the candidate diseases using each of the plurality of patient findings, thereby obtaining modified parameters representing modified estimated probabilities of the candidate diseases; and (d) outputting a candidate disease list capable of being displayed, the candidate disease list including one or more of the candidate diseases having highest modified estimated probabilities.

The invention additionally features a physical computing device programmed with executable instructions for directing the device to implement a method including the steps of: (a) providing, in the computing device, a representation of a set of candidate diseases and associated initial parameters representing estimated probabilities of the candidate diseases; (b) receiving, in the computing device, a plurality of patient findings for a patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations for one or more parents, siblings, or other family members; (c) iteratively modifying the initial parameters representing estimated probabilities of the candidate diseases using each of the plurality of patient findings, thereby obtaining modified parameters representing modified estimated probabilities of the candidate diseases; and (d) outputting a candidate disease list capable of being displayed, the candidate disease list including one or more of the candidate diseases having highest modified estimated probabilities.

In some embodiments of the computer readable medium or the physical computing device, step (c) includes using a Bayesian method to obtain the modified parameters representing modified estimated probabilities of the candidate diseases.

In some embodiments of the computer readable medium or the physical computing device, step (a) includes providing, in the computing device, a first set of quantities representing estimated probabilities of a plurality of patient findings in the general non-diseased population, and a second set of quantities representing estimated probabilities of a plurality of patient findings each assuming the presence of a specified candidate disease; and step (c) includes using the first set of quantities and second set of quantities of step (a) to iteratively modify the initial parameters representing estimated probabilities of the candidate diseases using each of the plurality of patient findings, thereby obtaining the modified parameters representing the modified estimated probabilities of the candidate diseases. For example, the one or more severity scores for each genetic variant identified may be used to modify one of the first set of quantities, the one of the first set of quantities representing an estimated probability of an abnormal gene with the genetic variant in the general non-diseased population. In particular, in some embodiments, a higher severity score for the genetic variant results in a lower one of the first set of quantities representing an estimated probability of the abnormal gene with the genetic variant in the general non-diseased population.

In some embodiments of the computer readable medium or the physical computing device, the genetic sequencing information associated with the patient includes identification of a plurality of genetic variants each associated with the same gene, and the genetic variant having the highest severity score among the genetic variants each associated with the gene is used to modify one of the first set of quantities representing the estimated probability of the abnormal gene corresponding to the genetic variant absent information about the presence of a specified candidate disease.

In some embodiments of the computer readable medium or the physical computing device, the severity score corresponding to each genetic variant is calculated by the computing device as a quantitative result from a plurality of inputs. The plurality of inputs may include, e.g., variant information from one or more other individuals, e.g., parents, siblings, or other family members of the patient. In some embodiments, the plurality of inputs includes an input selected from the group consisting of: zygosity in one or more other family members sequenced, frequency of the genetic variant in the general population, chromosome location, type of the genetic variant, functional score, conservation score, splice prediction score, depth of read score, read quality score, and score based on whether the genetic variant is known to cause disease. In some embodiments, the plurality of inputs includes a pathogenicity model selected from the group consisting of a loss of function pathogenicity model and a gain of function pathogenicity model.

In some embodiments of the computer readable medium or the physical computing device, the patient findings include, for at least one of the genetic variants identified, or for each of the genetic variants identified, both a monoallelic severity score and a biallelic severity score. For example, the monoallelic severity score may be used when the corresponding genetic variant is considered to cause a monoallelic disease, and the biallelic severity score may be used when the corresponding genetic variant is considered to cause a biallelic disease. In some embodiments, the monoallelic severity score is reduced, relative to the biallelic severity score, when the frequency of the corresponding genetic variant exceeds a threshold percentage of the population, e.g., 0.005%, 0.01%, 0.02%, 0.05%, 0.1%, 0.2%, 0.5%, 1%, 2%, or 5%.

In some embodiments of the computer readable medium or the physical computing device, the measure of zygosity for each genetic variant identified is a measure of the fraction of sequenced genetic material that includes the genetic variant. For example, the measure of zygosity for each genetic variant may be used to categorize the genetic variant as autosomal monoallelic, autosomal biallelic, X-linked monoallelic, X-linked biallelic, Y-linked, or mitochondrial. In addition, the genetic sequencing information associated with the patient may include identification of two genetic variants each associated with the same gene, the two genetic variants each having monoallelic zygosity and the gene being associated with a recessive disease, and wherein the two genetic variants are collectively categorized as possibly having compound heterozygosity. In some embodiments, the two genetic variants are collectively categorized as having a severity score corresponding to the lesser of the severity scores of the two genetic variants. In some embodiments, the genetic sequencing information associated with the patient includes identification of more than two genetic variants each associated with the same gene, the more than two genetic variants each having monoallelic zygosity and the gene being associated with a recessive disease, and wherein the more than two genetic variants are collectively categorized as possibly having compound heterozygosity and having a severity score corresponding to the lesser of the highest two severity scores of the more than two genetic variants.

In some embodiments, the genetic sequencing information associated with the patient includes identification of two genetic variants each associated with the same gene, the two genetic variants each having monoallelic zygosity and the gene being associated with a recessive disease, wherein genetic sequencing information further includes chromosomal location of the genetic variants, and wherein, if the chromosomal location is the same for each of the two genetic variants, the two genetic variants are not categorized as having compound heterozygosity.

In some embodiments, at least one of the genetic variants is of previously unidentified phenotype, wherein the genetic sequencing information includes chromosomal location for the genetic variant, and wherein the measure of zygosity and the chromosomal location for the genetic variant are used to categorize the genetic variant as autosomal monoallelic, autosomal biallelic, X-linked monoallelic, X-linked biallelic, Y-linked, or mitochondrial.

In some embodiments of the computer readable medium or the physical computing device, the patient findings further include, for at least one of the genetic variants identified, or for each of the genetic variants identified, information about a parent, sibling, or other family member of the patient, e.g., the mother and/or father of the patient, the information including a measure of zygosity of the genetic variant in the family member, e.g., the mother and/or the father.

In some embodiments of the computer readable medium or the physical computing device, the information about the parent, sibling, or other family member of the patient, e.g., the mother and/or father, is used to eliminate at least one compound heterozygote possibility, thereby resulting in a refined determination of the severity score. In some embodiments, at least one genetic variant determined to be monoallelic in the patient is eliminated based on the presence of the monoallelic genetic variant in the mother or father.

In some embodiments of the computer readable medium or the physical computing device, both parents are unaffected; in other embodiments, one or both parents may be affected; and/or siblings or other family members, whether unaffected or affected, may also or alternatively be included in the analysis.

In some embodiments of the computer readable medium or the physical computing device, the patient findings include identification of 2, 5, 10, 20, 50, 100, 200, 500, 1,000, 2,000, or more genetic variants.

In some embodiments of the computer readable medium or the physical computing device, the patient findings further include information that is not obtained from genetic sequencing of genetic material from the patient. For example, the information that is not obtained from genetic sequencing of the genetic material from the patient may include, e.g., information about a symptom, sign, medical history, presence or absence of similar disease in one or more family members or others nearby, laboratory test result, clinical result, environmental factor, historical information, or demographic profile associated with the patient.

In some embodiments of the computer readable medium or the physical computing device, step (c) further includes calculating the pertinence of one or more of the patient findings in light of other patient findings; and step (d) further includes outputting a patient finding list capable of being displayed, the patient finding list including one or more of the patient findings displayed with their pertinence in light of other patient findings. For example, calculating the pertinence of one or more of the patient findings may be performed in light of all other of the patient findings received in the computing device, and the patient finding list may include one or more of the patient findings displayed with their pertinence in light of all other of the patient findings received in the computing device. In some embodiments, the one or more of the patient findings is one or more genetic variants.

In some embodiments of the computer readable medium or the physical computing device, step (d) includes transmitting the candidate disease list over the Internet or to a display device. For example, step (d) may further include outputting to the display device the modified estimated probabilities of the one or more candidate diseases having highest modified estimated probabilities in rank order. In particular, the computer readable medium or the physical computing device may further include steps (b)-(d) being performed at least twice, wherein the second time step (b) is performed, a different plurality of patient findings is received by the computing device, resulting in outputting to the display device different of the modified estimated probabilities of the one or more candidate diseases having highest modified estimated probabilities in rank order. For example, the different plurality of patient findings may include a further patient finding, or the further patient finding may replace a previous patient finding.

In some embodiments of the computer readable medium or the physical computing device, the method results in the diagnosis of the patient as having one of the candidate diseases having highest modified estimated probabilities.

In some embodiments, the method results in the identification of one or more genes as having highest pertinence. For example, this may result in the identification of one or more relationships between each gene and a corresponding known disease or new variant similar to the known disease. In some embodiments, the method results in the identification of two or more genes as having highest pertinence, wherein the identification of each of the two or more genes as having highest pertinence results in the identification of relationships between each gene and a corresponding known disease or new variant similar to the known disease, and wherein the method results in the diagnosis of the patient as having each the corresponding known disease or new variant similar to the known disease.

In some embodiments of the computer readable medium or the physical computing device, the physical computing device is accessed and operated over the Internet.

In some embodiments of the computer readable medium or the physical computing device, the associated initial parameters are estimated probabilities of the candidate diseases. For example, the modified parameters may be modified estimated probabilities of the candidate diseases.

The invention further features a method of diagnosing or treating a patient in need thereof, the method including the steps of: (a) accessing a physical computing device including a representation of a set of candidate diseases and associated initial parameters representing estimated probabilities of the candidate diseases, wherein: (i) the computing device receives a plurality of patient findings for the patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations for one or more parents, siblings, or other family members; and (ii) the computing device iteratively modifies the initial parameters representing estimated probabilities of the candidate diseases using each of the plurality of patient findings, thereby obtaining modified parameters representing modified estimated probabilities of candidate diseases; (b) receiving a candidate disease list capable of being displayed, the candidate disease list including one or more of the candidate diseases having highest modified estimated probabilities; (c) diagnosing the patient as having one of the candidate diseases having highest modified estimated probabilities, e.g., based at least in part on the candidate disease list of step (b); and (d) optionally treating the patient, e.g., by administering a pharmaceutical composition to the patient or performing a physical procedure on the patient, based on the diagnosis. For example, the method may further include conducting an examination of the patient and transmitting to the computing device at least one of the patient findings resulting from the examination of the patient.

The invention additionally features a method of treating a patient in need thereof, the method including the steps of: (a) accessing a physical computing device including a representation of a set of candidate diseases and associated initial parameters representing estimated probabilities of the candidate diseases, wherein: (i) the computing device receives a plurality of patient findings for the patient being diagnosed, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations, for one or more parents, siblings, or other family members; and (ii) the computing device iteratively modifies the initial parameters representing estimated probabilities of the candidate diseases using each of the plurality of patient findings, thereby obtaining modified parameters representing modified estimated probabilities of the candidate diseases; (b) receiving, from the physical computing device, a candidate disease list capable of being displayed, the candidate disease list including one or more of the candidate diseases having highest modified estimated probabilities; (c) diagnosing the patient as having one of the candidate diseases having highest modified estimated probabilities, e.g., based at least in part on the candidate disease list of step (b); and (d) treating the patient for one of the candidate diseases having highest modified estimated probabilities as determined in step (c). For example, the method may further include conducting an examination of the patient and transmitting to the computing device at least one of the patient findings resulting from the examination of the patient. In some embodiments, the treating of step (d) includes administering a pharmaceutical composition to the patient or performing a physical procedure on the patient.

In some embodiments, the method may include, e.g., before, during, or after step (c), performing one or more additional diagnostic procedures, e.g., clinical diagnostic procedures, to confirm or assess the diagnosis of the patient in step (c) as having one of the candidate diseases having highest modified estimated probabilities.

In some embodiments, step (a)(ii) of the method of diagnosing or the method of treating includes using a Bayesian method to obtain the modified parameters representing modified estimated probabilities of the candidate diseases.

In some embodiments, the method of diagnosing or the method of treating further includes: in step (a), providing, in the computing device, a first set of quantities representing estimated probabilities of a plurality of patient findings in the general non-diseased population, and a second set of quantities representing estimated probabilities of a plurality of patient findings each assuming the presence of a specified candidate disease; and in step (a)(ii), using the first set of quantities and second set of quantities of step (a) to iteratively modify the initial parameters representing estimated probabilities of the candidate diseases using each of the plurality of patient findings, thereby obtaining the modified parameters representing the modified estimated probabilities of the candidate diseases. For example, the one or more severity scores for each genetic variant identified may be used to modify one of the first set of quantities, the one of the first set of quantities representing an estimated probability of an abnormal gene with the genetic variant in the general non-diseased population. In particular, in some embodiments, a higher severity score for the genetic variant results in a lower one of the first set of quantities representing an estimated probability of the abnormal gene with the genetic variant in the general non-diseased population.

In some embodiments, the genetic sequencing information associated with the patient includes identification of a plurality of genetic variants each associated with the same gene, and the genetic variant having the highest severity score among the genetic variants each associated with the gene is used to modify one of the first set of quantities representing the estimated probability of the abnormal gene corresponding to the genetic variant absent information about the presence of a specified candidate disease.

In some embodiments, the severity score corresponding to each genetic variant is calculated by the computing device as a quantitative result from a plurality of inputs. The plurality of inputs may include, e.g., variant information from one or more other individuals, e.g., parents, siblings, or other family members of the patient. In some embodiments, the plurality of inputs includes an input selected from the group consisting of: zygosity in one or more other family members sequenced, frequency of the genetic variant in the general population, chromosome location, type of the genetic variant, functional score, conservation score, splice prediction score, depth of read score, read quality score, and score based on whether the genetic variant is known to cause disease. In some embodiments, the plurality of inputs includes a pathogenicity model selected from the group consisting of a loss of function pathogenicity model and a gain of function pathogenicity model.

In some embodiments, the patient findings include, for at least one of the genetic variants identified, or for each of the genetic variants identified, both a monoallelic severity score and a biallelic severity score. For example, the monoallelic severity score may be used when the corresponding genetic variant is considered to cause a monoallelic disease, and the biallelic severity score may be used when the corresponding genetic variant is considered to cause a biallelic disease. In some embodiments, the monoallelic severity score is reduced, relative to the biallelic severity score, when the frequency of the corresponding genetic variant exceeds a threshold percentage of the population, e.g., 0.005%, 0.01%, 0.02%, 0.05%, 0.1%, 0.2%, 0.5%, 1%, 2%, or 5%.

In some embodiments, the measure of zygosity for each genetic variant identified is a measure of the fraction of sequenced genetic material that includes the genetic variant. For example, the measure of zygosity for each genetic variant may be used to categorize the genetic variant as autosomal monoallelic, autosomal biallelic, X-linked monoallelic, X-linked biallelic, Y-linked, or mitochondrial. In addition, the genetic sequencing information associated with the patient may include identification of two genetic variants each associated with the same gene, the two genetic variants each having monoallelic zygosity and the gene being associated with a recessive disease, and wherein the two genetic variants are collectively categorized as possibly having compound heterozygosity. In some embodiments, the two genetic variants are collectively categorized as having a severity score corresponding to the lesser of the severity scores of the two genetic variants. In some embodiments, the genetic sequencing information associated with the patient includes identification of more than two genetic variants each associated with the same gene, the more than two genetic variants each having monoallelic zygosity and the gene being associated with a recessive disease, and wherein the more than two genetic variants are collectively categorized as possibly having compound heterozygosity and having a severity score corresponding to the lesser of the highest two severity scores of the more than two genetic variants.

In some embodiments, the genetic sequencing information associated with the patient includes identification of two genetic variants each associated with the same gene, the two genetic variants each having monoallelic zygosity and the gene being associated with a recessive disease, wherein genetic sequencing information further includes chromosomal location of the genetic variants, and wherein, if the chromosomal location is the same for each of the two genetic variants, the two genetic variants are not categorized as having compound heterozygosity.

In some embodiments, at least one of the genetic variants is of previously unidentified phenotype, wherein the genetic sequencing information includes chromosomal location for the genetic variant, and wherein the measure of zygosity and the chromosomal location for the genetic variant are used to categorize the genetic variant as autosomal monoallelic, autosomal biallelic, X-linked monoallelic, X-linked biallelic, Y-linked, or mitochondrial.

In some embodiments, the patient findings further include, for at least one of the genetic variants identified, or for each of the genetic variants identified, information about a parent, sibling, or other family member of the patient, e.g., the mother and/or father of the patient, the information including a measure of zygosity of the genetic variant in the family member, e.g., the mother and/or the father.

In some embodiments, the information about the parent, sibling, or other family member of the patient, e.g., the mother and/or father, is used to eliminate at least one compound heterozygote possibility, thereby resulting in a refined determination of the severity score. In some embodiments, at least one genetic variant determined to be monoallelic in the patient is eliminated based on the presence of the monoallelic genetic variant in the mother or father.

In some embodiments, both parents are unaffected; in other embodiments, one or both parents may be affected, and/or siblings or other family members, whether unaffected or affected, may also or alternatively be included in the analysis.

In some embodiments, the patient findings include identification of 2, 5, 10, 20, 50, 100, 200, 500, 1,000, 2,000, or more genetic variants.

In some embodiments, the patient findings further include information that is not obtained from genetic sequencing of genetic material from the patient. For example, the information that is not obtained from genetic sequencing of the genetic material from the patient may include, e.g., information about a symptom, sign, medical history, presence or absence of similar disease in one or more family members or others nearby, laboratory test result, clinical result, environmental factor, historical information, or demographic profile associated with the patient.

In some embodiments, step (a)(ii) further includes calculating the pertinence of one or more of the patient findings in light of other patient findings; and step (b) further includes outputting a patient finding list capable of being displayed, the patient finding list including one or more of the patient findings displayed with their pertinence in light of other patient findings. For example, calculating the pertinence of one or more of the patient findings may be performed in light of all other of the patient findings received in the computing device, and the patient finding list may include one or more of the patient findings displayed with their pertinence in light of all other of the patient findings received in the computing device. In some embodiments, the one or more of the patient findings is one or more genetic variants.

In some embodiments, step (b) includes transmitting the candidate disease list over the Internet or to a display device. For example, step (b) may further include outputting to the display device the modified estimated probabilities of the one or more candidate diseases having highest modified estimated probabilities in rank order. In particular, the method may further include steps (a)(i), (a)(ii), and (b) being performed at least twice, wherein the second time step (a)(i) is performed, a different plurality of patient findings is received by the computing device, resulting in outputting to the display device different of the modified estimated probabilities of the one or more candidate diseases having highest modified estimated probabilities in rank order. For example, the different plurality of patient findings may include a further patient finding, or the further patient finding may replace a previous patient finding.

In some embodiments, the method results in the identification of one or more genes as having highest pertinence. For example, this may result in the identification of one or more relationships between each gene and a corresponding known disease or new variant similar to the known disease. In some embodiments, the method results in the identification of two or more genes as having highest pertinence, wherein the identification of each of the two or more genes as having highest pertinence results in the identification of relationships between each gene and a corresponding known disease or new variant similar to the known disease, and wherein the method results in the diagnosis of the patient as having each the corresponding known disease or new variant similar to the known disease.

In some embodiments, the physical computing device is accessed and operated over the Internet.

In some embodiments, the associated initial parameters are estimated probabilities of the candidate diseases. For example, the modified parameters may be modified estimated probabilities of the candidate diseases.

In some embodiments of any of the methods described herein, the method further includes, before step (a), the steps of: obtaining a physical sample from the patient, and optionally from a parent, a sibling, or another family member, that includes genetic material; conducting a sequencing analysis, e.g., including whole-genome sequencing or whole-exome sequencing, using the genetic material; obtaining, from the sequencing analysis, the genetic sequencing information associated with the patient; and providing the genetic sequencing information to the computing device.

The invention additionally features a method including providing, in a physical computing device, a representation of a set of candidate diseases and associated initial parameters representing estimated probabilities of the candidate diseases, wherein: (i) the computing device receives a plurality of patient findings for a patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations, for one or more parents, siblings, or other family members; (ii) the computing device iteratively modifies the initial parameters representing estimated probabilities of the candidate diseases using each of the plurality of patient findings, thereby obtaining modified parameters representing modified estimated probabilities of the candidate diseases; and (iii) the computing device outputs a candidate disease list capable of being displayed, the candidate disease list including one or more of the candidate diseases having highest modified estimated probabilities.

In some embodiments, step (ii) of the method includes using a Bayesian method to obtain the modified parameters representing modified estimated probabilities of the candidate diseases.

In some embodiments, the method further includes: providing, in the computing device, a first set of quantities representing estimated probabilities of a plurality of patient findings in the general non-diseased population, and a second set of quantities representing estimated probabilities of a plurality of patient findings each assuming the presence of a specified candidate disease, wherein, in step (ii), the computing device uses the first set of quantities and second set of quantities to iteratively modify the initial parameters representing estimated probabilities of the candidate diseases using each of the plurality of patient findings, thereby obtaining the modified parameters representing the modified estimated probabilities of the candidate diseases. For example, the one or more severity scores for each genetic variant identified may be used to modify one of the first set of quantities, the one of the first set of quantities representing an estimated probability of an abnormal gene with the genetic variant in the general non-diseased population. In particular, in some embodiments, a higher severity score for the genetic variant results in a lower one of the first set of quantities representing an estimated probability of the abnormal gene with the genetic variant in the general non-diseased population.

In some embodiments, the genetic sequencing information associated with the patient includes identification of a plurality of genetic variants each associated with the same gene, and the genetic variant having the highest severity score among the genetic variants each associated with the gene is used to modify one of the first set of quantities representing the estimated probability of the abnormal gene corresponding to the genetic variant absent information about the presence of a specified candidate disease.

In some embodiments, the severity score corresponding to each genetic variant is calculated by the computing device as a quantitative result from a plurality of inputs. The plurality of inputs may include, e.g., variant information from one or more other individuals, e.g., parents, siblings, or other family members of the patient. In some embodiments, the plurality of inputs includes an input selected from the group consisting of: zygosity in one or more other family members sequenced, frequency of the genetic variant in the general population, chromosome location, type of the genetic variant, functional score, conservation score, splice prediction score, depth of read score, read quality score, and score based on whether the genetic variant is known to cause disease. In some embodiments, the plurality of inputs includes a pathogenicity model selected from the group consisting of a loss of function pathogenicity model and a gain of function pathogenicity model.

In some embodiments, the patient findings include, for at least one of the genetic variants identified, or for each of the genetic variants identified, both a monoallelic severity score and a biallelic severity score. For example, the monoallelic severity score may be used when the corresponding genetic variant is considered to cause a monoallelic disease, and the biallelic severity score may be used when the corresponding genetic variant is considered to cause a biallelic disease. In some embodiments, the monoallelic severity score is reduced, relative to the biallelic severity score, when the frequency of the corresponding genetic variant exceeds a threshold percentage of the population, e.g., 0.005%, 0.01%, 0.02%, 0.05%, 0.1%, 0.2%, 0.5%, 1%, 2%, or 5%.

In some embodiments, the measure of zygosity for each genetic variant identified is a measure of the fraction of sequenced genetic material that includes the genetic variant. For example, the measure of zygosity for each genetic variant may be used to categorize the genetic variant as autosomal monoallelic, autosomal biallelic, X-linked monoallelic, X-linked biallelic, Y-linked, or mitochondrial. In addition, the genetic sequencing information associated with the patient may include identification of two genetic variants each associated with the same gene, the two genetic variants each having monoallelic zygosity and the gene being associated with a recessive disease, and wherein the two genetic variants are collectively categorized as possibly having compound heterozygosity. In some embodiments, the two genetic variants are collectively categorized as having a severity score corresponding to the lesser of the severity scores of the two genetic variants. In some embodiments, the genetic sequencing information associated with the patient includes identification of more than two genetic variants each associated with the same gene, the more than two genetic variants each having monoallelic zygosity and the gene being associated with a recessive disease, and wherein the more than two genetic variants are collectively categorized as possibly having compound heterozygosity and having a severity score corresponding to the lesser of the highest two severity scores of the more than two genetic variants.

In some embodiments, the genetic sequencing information associated with the patient includes identification of two genetic variants each associated with the same gene, the two genetic variants each having monoallelic zygosity and the gene being associated with a recessive disease, wherein genetic sequencing information further includes chromosomal location of the genetic variants, and wherein, if the chromosomal location is the same for each of the two genetic variants, the two genetic variants are not categorized as having compound heterozygosity.

In some embodiments, at least one of the genetic variants is of previously unidentified phenotype, wherein the genetic sequencing information includes chromosomal location for the genetic variant, and wherein the measure of zygosity and the chromosomal location for the genetic variant are used to categorize the genetic variant as autosomal monoallelic, autosomal biallelic, X-linked monoallelic, X-linked biallelic, Y-linked, or mitochondrial.

In some embodiments, the patient findings further include, for at least one of the genetic variants identified, or for each of the genetic variants identified, information about a parent, sibling, or other family member of the patient, e.g., the mother and/or father of the patient, the information including a measure of zygosity of the genetic variant in the family member, e.g., the mother and/or the father.

In some embodiments, the information about the parent, sibling, or other family member of the patient, e.g., the mother and/or father, is used to eliminate at least one compound heterozygote possibility, thereby resulting in a refined determination of the severity score. In some embodiments, at least one genetic variant determined to be monoallelic in the patient is eliminated based on the presence of the monoallelic genetic variant in the mother or father.

In some embodiments, both parents are unaffected; in other embodiments, one or both parents may be affected, and/or siblings or other family members, whether unaffected or affected, may also or alternatively be included in the analysis.

In some embodiments, the patient findings include identification of 2, 5, 10, 20, 50, 100, 200, 500, 1,000, 2,000, or more genetic variants.

In some embodiments, the patient findings further include information that is not obtained from genetic sequencing of genetic material from the patient. For example, the information that is not obtained from genetic sequencing of the genetic material from the patient may include, e.g., information about a symptom, sign, medical history, presence or absence of similar disease in one or more family members or others nearby, laboratory test result, clinical result, environmental factor, historical information, or demographic profile associated with the patient.

In some embodiments, step (ii) further includes the computing device calculating the pertinence of one or more of the patient findings in light of other patient findings; and step (iii) further includes the computing device outputting a patient finding list capable of being displayed, the patient finding list including one or more of the patient findings displayed with their pertinence in light of other patient findings. For example, calculating the pertinence of one or more of the patient findings may be performed in light of all other of the patient findings received in the computing device, and the patient finding list may include one or more of the patient findings displayed with their pertinence in light of all other of the patient findings received in the computing device. In some embodiments, the one or more of the patient findings is one or more genetic variants.

In some embodiments, step (iii) includes the computing device transmitting the candidate disease list over the Internet or to a display device. For example, step (iii) may further include the computing device outputting to the display device the modified estimated probabilities of the one or more candidate diseases having highest modified estimated probabilities in rank order. In particular, the method may further include steps (i)-(iii) being performed at least twice, wherein the second time step (i) is performed, a different plurality of patient findings is received by the computing device, resulting in outputting to the display device different of the modified estimated probabilities of the one or more candidate diseases having highest modified estimated probabilities in rank order. For example, the different plurality of patient findings may include a further patient finding, or the further patient finding may replace a previous patient finding.

In some embodiments, the method results in the diagnosis of the patient as having one of the candidate diseases having highest modified estimated probabilities.

In some embodiments, the method results in the identification of one or more genes as having highest pertinence. For example, this may result in the identification of one or more relationships between each gene and a corresponding known disease or new variant similar to the known disease. In some embodiments, the method results in the identification of two or more genes as having highest pertinence, wherein the identification of each of the two or more genes as having highest pertinence results in the identification of relationships between each gene and a corresponding known disease or new variant similar to the known disease, and wherein the method results in the diagnosis of the patient as having each the corresponding known disease or new variant similar to the known disease.

In some embodiments, the physical computing device is accessed and operated over the Internet.

In some embodiments, the associated initial parameters are estimated probabilities of the candidate diseases. For example, the modified parameters may be modified estimated probabilities of the candidate diseases.

The invention further features use of compound heterozygosity analysis and/or comparison to parents, siblings, or other family members of the patient, not only to analyze genes with described or well-characterized clinical findings, but also for genes with no clinical findings or poorly-described clinical findings. For example, a list of genes with no described clinical findings, and associated calculated severity scores, may be outputted based on such an analysis, which may help, e.g., prioritize research on one or more of these genes.

Accordingly, the invention further features a method including the steps of: (a) receiving, in a physical computing device, a plurality of patient findings for a patient being diagnosed, wherein the patient findings include genetic sequencing information associated with the patient including identification of one or more genetic variants associated with a gene, and for each genetic variant identified, a corresponding severity score and measure of zygosity for the patient; (b) using the measure of zygosity for each genetic variant to categorize the one or more genetic variants, in the computing device, as autosomal monoallelic, autosomal biallelic, X-linked monoallelic, X-linked biallelic, Y-linked, or mitochondrial; (c) using the computing device to identify two or more genetic variants each associated with the same gene, the two genetic variants each having monoallelic zygosity, wherein the two or more genetic variants are collectively categorized as possibly having compound heterozygosity; (d) using the computing device to determine a combined severity score for the gene in step (c) corresponding to the lesser of the highest two severity scores of the two or more genetic variants in step (c); (e) repeating steps (c) and (d) for each gene having two or more associated genetic variants; and (f) outputting a list including all or a subset of: (i) each gene having an associated genetic variant identified in step (a), and: (ii) for each gene having two or more genetic variants identified in step (c), the combined severity score associated with the gene determined in step (d); and for each gene having only one genetic variant identified in step (a), the severity score associated with the genetic variant, wherein the list includes genes with no previously described clinical findings, and wherein the list is capable of being displayed.

In some embodiments, the patient findings further include, for each of the genetic variants identified, information about a parent, sibling, or other family member of the patient, the information including a measure of zygosity of the genetic variant in the family member. For example, the patient findings may further include, for each of the genetic variants identified, information about the mother and the father of the patient, the information including a measure of zygosity of the genetic variant in each of the mother and the father. In some embodiments, the information about the mother and the father of the patient is used to eliminate at least one compound heterozygote possibility, thereby resulting in a refined determination of the combined severity score. In some embodiments, at least one genetic variant determined to be monoallelic in the patient is eliminated based on the presence of the monoallelic genetic variant in the mother or father.

In some embodiments, the patient findings include, for each of the genetic variants identified, both a monoallelic severity score and a biallelic severity score. For example, step (d) may include determining a combined biallelic severity score for the gene in step (c) corresponding to the lesser of the highest two biallelic severity scores of the two or more genetic variants in step (c). In some embodiments, the method further includes determining, for each gene, an overall monoallelic severity score corresponding to the highest monoallelic severity score of the one or more genetic variants associated with the gene that are not eliminated based on the presence of the monoallelic genetic variant in the mother or father. In some embodiments, the severity score outputted for each gene in the list is the greater of the overall monoallelic severity score and the combined biallelic severity score.

The invention further features devices and systems for practicing the methods described herein. For example, the invention further features a computer readable medium having stored thereon executable instructions for directing a physical computing device to implement a method including the steps of: (a) receiving, in the physical computing device, a plurality of patient findings for a patient being diagnosed, wherein the patient findings include genetic sequencing information associated with the patient including identification of one or more genetic variants associated with a gene, and for each genetic variant identified, a corresponding severity score and measure of zygosity for the patient; (b) using the measure of zygosity for each genetic variant to categorize the one or more genetic variants, in the computing device, as autosomal monoallelic, autosomal biallelic, X-linked monoallelic, X-linked biallelic, Y-linked, or mitochondrial; (c) using the computing device to identify two or more genetic variants each associated with the same gene, the two genetic variants each having monoallelic zygosity, wherein the two or more genetic variants are collectively categorized as possibly having compound heterozygosity; (d) using the computing device to determine a combined severity score for the gene in step (c) corresponding to the lesser of the highest two severity scores of the two or more genetic variants in step (c); (e) repeating steps (c) and (d) for each gene having two or more associated genetic variants; and (f) outputting a list including all or a subset of: (i) each gene having an associated genetic variant identified in step (a), and: (ii) for each gene having two or more genetic variants identified in step (c), the combined severity score associated with the gene determined in step (d); and for each gene having only one genetic variant identified in step (a), the severity score associated with the genetic variant, wherein the list includes genes with no previously described clinical findings, and wherein the list is capable of being displayed.

The invention additionally features a physical computing device programmed with executable instructions for directing the device to implement a method including the steps of: (a) receiving, in the physical computing device, a plurality of patient findings for a patient being diagnosed, wherein the patient findings include genetic sequencing information associated with the patient including identification of one or more genetic variants associated with a gene, and for each genetic variant identified, a corresponding severity score and measure of zygosity for the patient; (b) using the measure of zygosity for each genetic variant to categorize the one or more genetic variants, in the computing device, as autosomal monoallelic, autosomal biallelic, X-linked monoallelic, X-linked biallelic, Y-linked, or mitochondrial; (c) using the computing device to identify two or more genetic variants each associated with the same gene, the two genetic variants each having monoallelic zygosity, wherein the two or more genetic variants are collectively categorized as possibly having compound heterozygosity; (d) using the computing device to determine a combined severity score for the gene in step (c) corresponding to the lesser of the highest two severity scores of the two or more genetic variants in step (c); (e) repeating steps (c) and (d) for each gene having two or more associated genetic variants; and (f) outputting a list including all or a subset of: (i) each gene having an associated genetic variant identified in step (a), and: (ii) for each gene having two or more genetic variants identified in step (c), the combined severity score associated with the gene determined in step (d); and for each gene having only one genetic variant identified in step (a), the severity score associated with the genetic variant, wherein the list includes genes with no previously described clinical findings, and wherein the list is capable of being displayed.

Any of the embodiments described herein may be used in conjunction with any of the methods, devices, or systems described herein.

By "associated initial parameter representing estimated probability of a candidate disease" is meant an a priori probability, or a parameter representing same, e.g., of occurrence of a candidate disease in the general population absent knowledge of specific patient findings. An initial parameter may be, e.g., directly proportional to an estimated probability, or otherwise related to the estimated probability in a defined manner that facilitates computation. In an alternative embodiment, the associated initial parameters may be set to other values, e.g., they may all be set to the same default value, an option useful, e.g., to model a tertiary referral scenario in which people with common diseases are less likely to be referred than people with less common diseases.

By "candidate disease" is meant any disease, disorder, or other medical condition known in the art that is represented in a database used in the methods and devices described herein.

By "clinical or laboratory information" in the context of information gathered about a patient is meant information obtained either in a clinical setting, e.g., by examination, inquiry, or analysis by a medical professional, or obtained in a laboratory setting, e.g., the result of a laboratory test.

By "genetic sequencing information" is meant information obtained from, e.g., whole-exome sequencing, whole-genome sequencing, or other methods of sequencing a plurality of genes of the patient or other relevant areas of the genome.

By "genetic variant" is meant a mutation in a specified region of the patient's genome. In some instances, a genetic variant that is considered by the methods, devices, and systems described herein will occur within the coding region of a gene, but genetic variants may also occur in non-coding regions of the genetic material, e.g., in upstream regions, downstream regions, or within introns. A genetic variant may include any type of mutation, e.g., an insertion, deletion, or substitution mutation. A particular gene may have more than one genetic variant associated with it. For example, if sequencing detects a first mutation of a gene in one sequenced region and a second mutation of the same gene in a second sequenced region, each mutation is typically treated as a separate genetic variant.

By "highest pertinence" for one or more findings is meant that the one or more findings are among a set of findings having the largest pertinence measures for a given context, e.g., within the top 1, 2, 3, 4, 5, 6, 7, 8, 9, or 10 findings having the largest pertinence measures in that context.

By "highest probability" for one or more candidate diseases is meant that the one or more candidate diseases are among a set of candidate diseases having the largest probabilities for a given context, e.g., within the top 1, 2, 3, 4, 5, 6, 7, 8, 9, or 10 candidate diseases having the largest probabilities, e.g., largest modified estimated probabilities, in that context.

By "measure of zygosity" in the context of a genetic variant is meant a measure of the fraction of sequenced genetic material that includes the genetic variant. The measure of zygosity may be used to categorize the genetic variant, e.g., as autosomal monoallelic, autosomal biallelic, X-linked monoallelic, X-linked biallelic, Y-linked, or mitochondrial. In some embodiments, if the fraction of sequenced genetic material that includes the genetic variant is below a threshold level, e.g., below 0.2, the genetic variant is deemed to be absent; if the fraction is within a specified range, e.g., 0.2-0.8, the genetic variant is deemed to be heterozygous, e.g., autosomal monoallelic, or X-linked monoallelic in a female; and if the fraction is above a threshold level, e.g., above 0.8, the genetic variant is deemed to be homozygous (where two copies are present, e.g., for an autosomal biallelic or X-linked biallelic gene) or hemizygous (where one copy is present, e.g., X-linked monoallelic for a male).

By "modified parameter representing modified estimated probability of a candidate disease" is meant an a posteriori probability, or a parameter representing same, of occurrence of a candidate disease in a patient having taken into account available patient findings. A modified parameter may be, e.g., directly proportional to a modified estimated probability, or otherwise related to the modified estimated probability in a defined manner that facilitates computation.

By "patient finding" is meant, for example, information obtained from genetic sequencing of genetic material from the patient, or other information associated with the patient that may facilitate a diagnosis or treatment. Information obtained from genetic sequencing can include, e.g., partial or complete results of whole-exome sequencing, whole-genome sequencing, or other methods of sequencing a plurality of genes of the patient. In some embodiments, sequencing results in the generation of a genetic variant table, which may include, for each genetic variant identified, a gene name or extra-genic location, one or more severity scores, and a corresponding measure of zygosity in the patient, and optionally in the patients' parents, siblings, or other family members.

Patient findings may also include information that is not obtained from genetic sequencing of genetic material from the patient. Examples of such information are information about a symptom, sign, medical history, presence or absence of similar disease in one or more family members or others nearby, laboratory test result, clinical result, environmental factor, historical information, or demographic profile associated with the patient.

By "pertinence" is meant the degree to which a finding is important in influencing the diagnostic or treatment possibilities, commonly used in medicine as "pertinent positives" and "pertinent negatives" for pertinent findings present or absent, but here having a specific meaning in terms of the ability to compute the influence of presence or absence of the finding on the diseases in the differential diagnosis. In some embodiments, pertinence may be calculated in accordance with the systems and methods of determining usefulness of a test as yet not performed (described, for example, in U.S. Pat. No. 6,754,655, incorporated by referenced herein in its entirety and at col. 7, line 3, to col. 9, line 4), except applied retrospectively to a test already performed instead of prospectively to a test not yet performed. See, e.g., the further description provided below under the heading "Pertinence." By "pharmaceutically acceptable carrier" or "pharmaceutically acceptable excipient" is meant a carrier or excipient that is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in Remington: The Science and Practice of Pharmacy ($21^{st}$ edition), 2005, Lippincott, Williams & Wilkins, Philadelphia, Pa.

By "pharmaceutical composition" is meant a compound formulated with a pharmaceutically acceptable excipient and manufactured or sold with the approval of a governmental regulatory agency as part of a therapeutic regimen for the treatment or prevention of a disease or event in a subject. Pharmaceutical compositions can be formulated, for example, for oral administration (e.g., a tablet, capsule, caplet, gelcap, or syrup), intravenous administration (e.g., as a sterile solution free of particulate emboli and in a solvent system suitable for intravenous use), subcutaneous administration, or any other formulation known in the art, e.g., in unit dosage form.

By "severity score" in the context of a genetic variant is meant a measure of the severity of disease or other clinical manifestation predicted for that genetic variant based on the observed change in the gene sequence. In some embodiments this is based on understanding of protein structure, for example whether a mutation would truncate the protein or substitute a different amino acid in a crucial region, and in other embodiments this is based on consulting records of clinical outcomes in people with that type of mutation. In some embodiments, a severity score of predetermined value, e.g., an integer between 0 and 4 inclusive, may be assigned to each genetic variant detected in sequencing, where, for example, 0 represents the lowest severity and 4 represents the highest severity. In other embodiments, severity score may be calculated as a quantitative result, not necessarily limited to a small discrete set of possible values as described above, e.g., by weighing one or more inputs from sequencing and bioinformatics analysis. In some embodiments two severity scores are calculated for each variant, tailored for monoallelic and biallelic situations, and the relevant version is used based on other variants found in the patient and whether known diseases and known zygosity in other family members suggest monoallelic or biallelic disease.

By "treating," "treat," or "treatment" is meant the medical management of a patient with the intent to cure, ameliorate, stabilize, reduce the likelihood of, or prevent a disease, pathological condition, disorder, or event, e.g., by administering a pharmaceutical composition or performing a physical procedure, e.g., a surgical or other medical procedure, on the patient. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief of symptoms rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event. In addition, the term includes actions taken by the parent to prevent conception, implantation or birth of other children with the same genetic disease.

Any of the methods, devices, or systems described herein may be used, e.g., by a clinician, in the diagnosis and/or treatment of a patient in need thereof.

Other features and advantages of the invention will be apparent from the detailed description and from the claims.

BRIEF DESCRIPTION OF THE DRAWINGS

FIG. 1 is an illustrative variant table with added comments.

FIG. 2 is a screen shot showing the display after importing a genome variant table but no clinical findings.

FIG. 3 is a screen shot after entering clinical findings but no genome information.

FIG. 4 is a screen shot after both entering clinical findings and importing a genome variant table.

FIG. 5 is a screen showing the process of setting parameters relating to computing severity scores from bioinformatics inputs.

FIG. 6 is a screen shot showing the process of defining a finding in the database.

FIG. 7 is a screen showing the ability to apply different inheritance modes based on chromosomal location, even for genes with no known human phenotype.

FIG. 8 is a screen shot showing that, in comparison to FIG. 4, using different findings results in a different differential diagnosis and different pertinence for the genes.

FIG. 9 is a screen shot showing that, in comparison to FIG. 8, a lower severity SCN1A mutation reduces the probability of SCN1A related diseases such as Dravet syndrome and lowers the pertinence of the SCN1A gene mutation.

FIG. 10 is a screen shot showing the power of the pertinence measure in picking out the presence of two coexisting diagnoses.

FIG. 11 is an illustrative variant table that includes not only information about the patient but about both parents as well.

FIG. 12 is the display of variants of a gene from a patient, shaded to indicate the variants that could contribute to the severity score assigned to the gene.

DETAILED DESCRIPTION OF THE INVENTION

The present invention features methods, devices, and systems, e.g., for diagnosing or treating a patient in need thereof or for providing decision support that enables or facilitates diagnosis or treatment.

In one exemplary implementation, a method of the invention includes the steps of:

(a) providing, in a physical computing device, a representation of a set of candidate diseases and associated initial parameters representing estimated probabilities of said candidate diseases;

(b) receiving, in the computing device, a plurality of patient findings for the patient being diagnosed or treated, wherein each patient finding is representative of clinical or laboratory information gathered about the patient, and wherein the patient findings include genetic sequencing information associated with the patient including identification of one or more genetic variants, and for each genetic variant identified, one or more corresponding severity scores and a corresponding measure of zygosity for the patient, and optionally in some implementations, for one or more parents, siblings, or other family members;

(c) using the computing device to iteratively modify the initial parameters representing estimated probabilities of the candidate diseases using each of the plurality of patient findings, thereby obtaining modified parameters representing modified estimated probabilities of the candidate diseases; and (d) outputting a candidate disease list capable of being displayed, the candidate disease list including one or more of the candidate diseases having highest modified estimated probabilities, and optionally further outputting a list of one or more genes having highest measures of pertinence.

Other methods, devices, and systems are described herein.

The methods, devices, and systems described herein are capable of integrating genome sequencing with automated comparison to known "phenotypes" (clinical and laboratory abnormalities) of diseases. The large assemblage of these phenotypes is referred to as the "phenome"; thus, the integrated process is referred to herein as an "automated genome-phenome analysis."

In some instances, processing genome information may be divided into three stages: sequencing, bioinformatics, and automated genome-phenome analysis.

Stage 1: Sequencing

Any method of sequencing known in the art, e.g., next-generation methods of sequence analysis such as whole-genome sequencing or whole-exome sequencing, may be used to generate sequence information. Typically, a sample containing the patient's DNA is obtained; the DNA is broken into many fragments, each typically smaller than a gene; and the sequence of each fragment is determined and reported.

Stage 2: Bioinformatics

In this stage, the fragments are analyzed to yield, e.g., a variant table that includes the following information about variant sequences (sequences that differ from normals in the population):

a) Gene name: the standard alphanumeric code for the known gene in which the variant sequence occurs, or extra-genic location;

b) Zygosity: the fraction of sequences that contain the variant, with, e.g., closeness to 50% being interpreted as heterozygous, and closeness to 100% being interpreted as homozygous. This may be indicated only for the patient or also for parents or other family members who are affected or unaffected, and c) Severity score(s): prediction of the disruption of functioning caused by the variant sequence, with a deletion assigned a maximal severity score and lesser mutations assigned lesser scores; or information that can be used to compute a severity score, such as presence of deletions, or high number of variant reads; and optionally, computation of separate severity scores for monoallelic and biallelic situations, assigning, for example, a lower monoallelic severity score to a variant found in >0.1% of the population, a frequency implausibly high for a gene causing a monoallelic rare disease. However, 0.1% frequency is plausible for a gene causing a biallelic rare disease, since the frequency of the disease would be much lower due to two copies of the unusual gene variant being needed for expression of the disease.

A variant table may be used as an input to Stage 3, as described below. An illustrative example of a variant table is shown in the first four columns of the table in FIG. 1, which list the gene name ("HGNC symbol"), zygosity for the patient ("Proband %"), and severity score using monoallelic and biallelic models ("Mono Severity" and "Biallelic Severity"). Also included in the table of FIG. 1 are illustrative comments on the inheritance of relevant diseases ("Inheritance"; e.g., AD=autosomal dominant, AR=autosomal recessive, XR=X-linked recessive, and M=mitochondrial), and the interpretation of the meaning of the variant and the action taken by the software ("Interpretation"). For illustrative purposes, only a few variants are shown, but in the actual implementation the number of variants may be many thousands, illustrating the need for systems and methods of performing the genome-phenome analysis.

Stage 3: Automated Genome-Phenome Analysis

The methods, devices, and systems described here may receive as input, e.g., a variant table, and optionally the patient's clinical findings, and use this information to compute the probability of various diseases, including but not limited to:

a) Genetic diseases, based, e.g., on information from Stages 1 and 2;

b) Genetic diseases missed by the fragment-type sequencing, e.g., diseases with abnormal numbers of trinucleotide repeats, which are not well reported by sequencing of small fragments of DNA, and large copy number variants; and c) Non-genetic diseases, for which the genome information is not relevant, except for its failure to make a plausible case for a genetic disease.

The methods, devices, and systems described herein go beyond the list-based approaches used in other tools, instead allowing the clinician to combine information about genetic variants and clinical findings to calculate a quantitative estimate of probability of diseases that incorporates both genomic information and clinical findings, including both pertinent positive and negative findings, with clinical findings including historical information, signs observed on examination, and laboratory and imaging information. For each disease, factors such as incidence, treatability, and family history may be taken into account, and for each finding in each disease, factors such as frequency, age of onset, and age of disappearance may be taken into account. The methods, devices, and systems described herein further enable clinicians to specify whether each finding is required to be a known feature of the diagnoses suggested.

Using the methods, devices, and systems of the present invention results in substantially increased accuracy and efficiency in diagnosing or treating a patient. Furthermore, it places a patient's genetic abnormalities in the context of the diseases with abnormalities in those genes, as well as in the context of other known diseases, including genetic diseases for which DNA fragment testing is not informative and non-genetic diseases that need to be considered as well.

The benefits of the methods, devices, and systems described herein are not just a one-time improvement in analysis. The automated process adds the powerful ability to re-analyze the data as information changes. For example, any of the following three types of information may change:

1. The database of findings in diseases, including genes associated with diseases and the non-genetic findings in diseases. All of these many be updated frequently as knowledge advances;

2. The clinical findings of the patient, which change as new clinical findings appear or are recognized or used to query the genomic data, and as other testing is done, e.g., blood tests or MRI scans; and 3. The variant table or other bioinformatics output, which can change with improved sequencing, with sequencing of further family members, and with improved bioinformatics capability.

As a result of the automated genome-phenome analysis made possible by the systems and methods described here, the analysis can be re-run, e.g., whenever any of these three forms of data change, making genomic information a living part of the medical care of patients.

Pertinence

The ability to rank genes by pertinence is of major significance in making genetic diagnoses. It is important even in the simple case in which only one gene is important in determining the diagnosis, since a measure of pertinence helps prioritize which genes should get most attention. However, it is even more important in cases in which more than one gene is involved. One of the long-recognized limitations of decision support for diagnosis is dealing with patients who have two or more different diagnoses. In such cases, the differential diagnosis is a mixture of two or more diseases, and no disease in the differential diagnosis can be recognized as providing an excellent match with all the patient's findings. However, applying the second metric of gene pertinence solves the two—(or more) diagnosis problem for genetic diseases, e.g., if a substantial fraction of a patient's genes have been sequenced. It does so by determining, for example, at least two genes with high pertinence by virtue of the power of the severity of the gene variants to change the differential diagnosis, as determined, for example, as follows.

As described in U.S. Pat. No. 6,754,655, hereby incorporated by reference:

$$U_{FDi}=|p_{F\ Present}*(\text{new }p_{Di}\text{ for }F\text{ present}-p_{Di})|+ |p_{F\ Absent}*(\text{new }p_{Di}\text{ for }F\text{ absent}-p_{Di})|$$

where:

$U_{FDi}$=usefulness of a finding F in diagnosing disease i $p_{F\ Present}$=probability that a finding is present (and similarly for absent)

$p_{Di}$=probability of disease i and the total usefulness of a finding is the summation of $U_{FDi}$ over all diseases.

A complexity in the calculation in U.S. Pat. No. 6,754,655 centered on the weighting based on $p_{F\ Present}$ and $p_{F\ Absent}$. Advantageously, in the retrospective version of usefulness, referred to herein as pertinence, the calculation is generally only made for the tens of findings that are present, not the thousands of possible findings. Furthermore, in a pertinence calculation, the relevant finding is known to be present, so it is not necessary to calculate $p_{F\ Present}$ and $p_{F\ absent}$.

Consequently, pertinence can be calculated as follows for a finding that is present:

$$P_{FDi}=|\text{new }p_{Di}\text{ for }F\text{ absent}-p_{Di}|$$

where:

$P_{FDi}$=pertinence of a finding F in diagnosing disease i and $p_{Di}$=probability of disease i.

As in U.S. Pat. No. 6,754,655, all increases in probability are balanced by decreases in probability, so pertinence terms are calculated using the terms in which the expression is positive:

$$P_{FDi}=\text{new }p_{Di}\text{ for }F\text{ absent}-p_{Di}$$

and the total pertinence of a finding is the summation of $P_{FDi}$ over all diseases, with the $p_{Di}$ terms calculated, e.g., as in U.S. Pat. No. 6,754,655, using Bayes' Theorem.

Use of a pertinence measure as described herein not only solves the two—(or more) diagnosis problem, it also solves the atypical diagnosis problem. If a disease is ranked low in the differential diagnosis, e.g. at #20, its gene will still rise high in pertinence if relevant gene variants are found, even if the typical clinical phenotype associated with the disease is not an exact match.

By applying this measure of pertinence to a "gold standard" metric for a disease, the relevant gene, pertinence of genes becomes a powerful tool for solving many of the most difficult problems in genetic diagnosis.

EXAMPLES

The following examples are provided for the purpose of illustrating the invention and are not meant to limit the invention in any way.

Example 1

Computing with Severity Scores

The methods, devices, and systems described herein may use severity scores to override the default probability assigned to the finding of an abnormal gene test. In one implementation, a high severity score of 4 is taken as probability of, e.g., 0.000001 of such a gene abnormality in "normals" (e.g., the general non-diseased population), while an intermediate severity score of 2 is taken as a probability of, e.g., 0.0001. As a result, the diagnostic software treats a variant with high severity score as being like a rare clinical or lab finding, which can influence the diagnosis dramatically, while it treats a variant with an intermediate severity score as being like a more common clinical or lab finding, which influences the diagnosis less. Severity scores may be, e.g., integers, e.g., 0-4 inclusive, or, in some embodiments, may be non-integer values.

Figure 2:
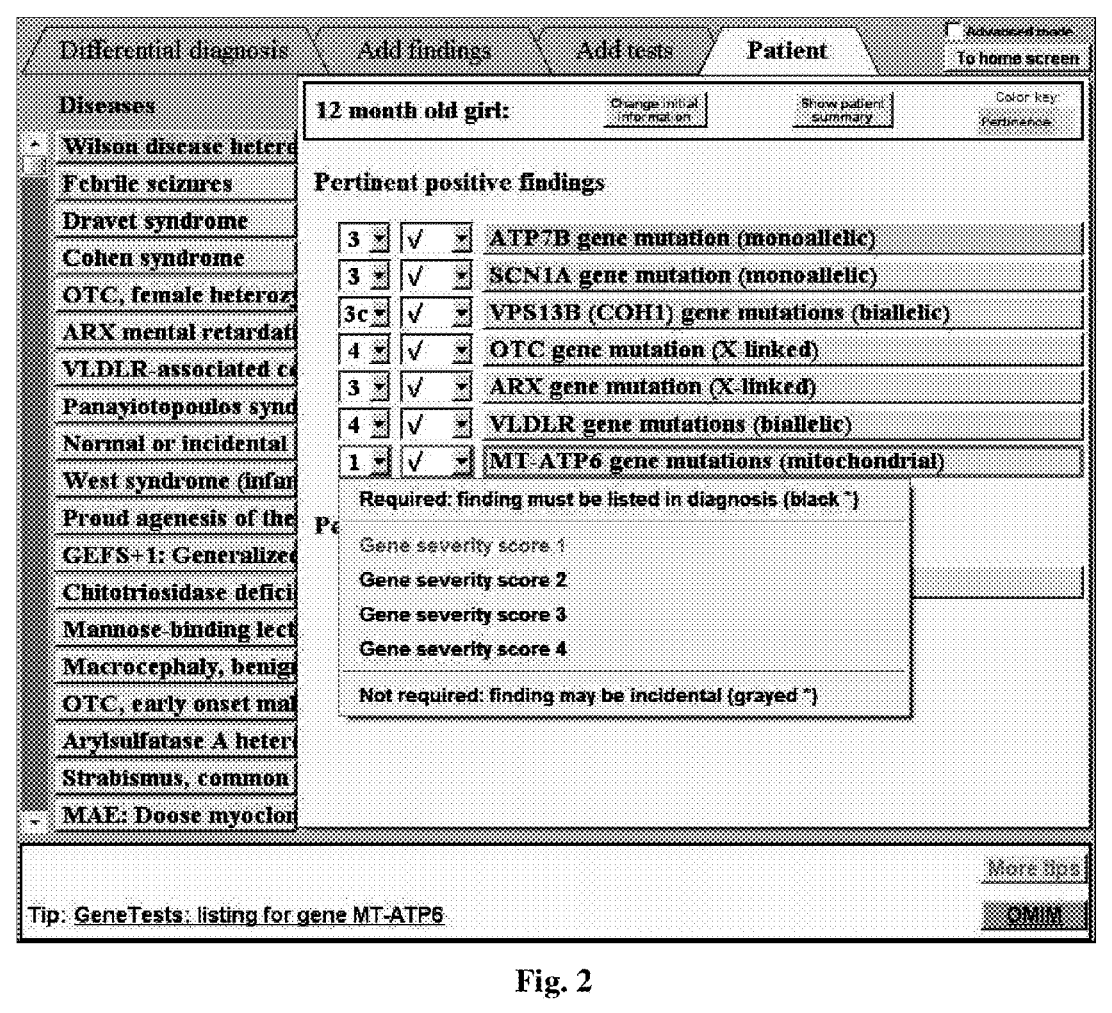

The importing of the variant table of FIG. 1 into the software, keeping the most severe variant for each gene, but not adding any clinical findings, is illustrated in FIG. 2. Note that for the SCN1A gene, of the three variants in FIG. 1, the software selects the one with the highest severity for that gene in the variant table, severity 3, as being the severity most relevant to disease (the 3 to the left of the SCN1A finding in FIG. 2 displays the severity score). FIG. 2 also illustrates the differential diagnosis (left side of figure), with a variety of diseases in the differential diagnosis relevant to the gene findings, with a very common condition, Wilson disease heterozygote, ranked highest chiefly because it is far more common than the other diseases listed. (Note the subtle background shading used to designate the probability distribution for diseases, with Wilson disease heterozygote having almost all the shading. Also, note the subtle background shading used to designate pertinence of findings, with ATP7B monoallelic gene mutation having the bulk of finding pertinence).

Figure 3:
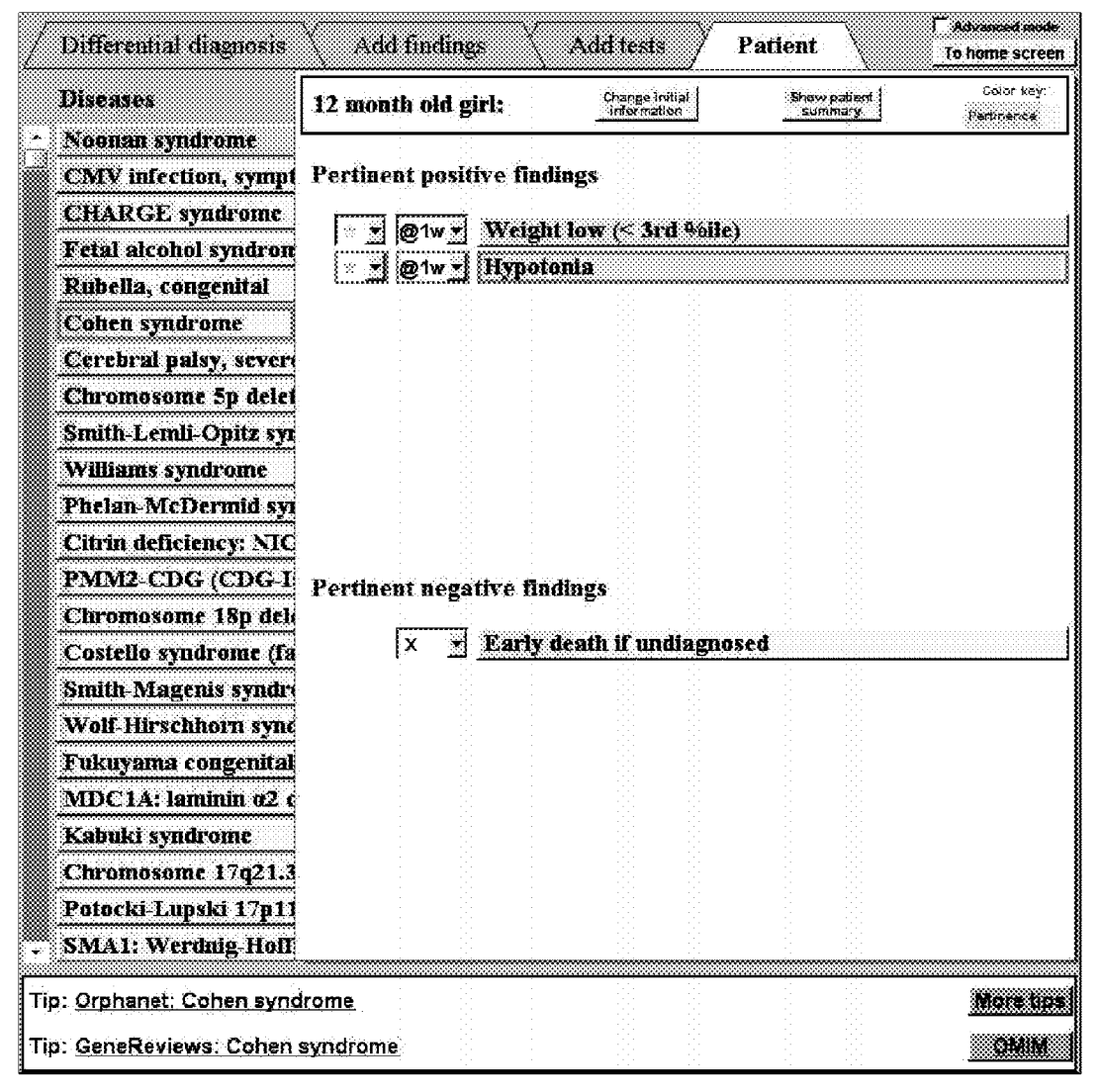

In contrast, FIG. 3 illustrates adding the patient's findings, including the clinical findings of low weight with onset at about 1 week of age and hypotonia with onset at about 1 week of age, but not importing genome data. Note that one disease, Cohen syndrome, is in the differential diagnosis on the basis of the genome alone (FIG. 2) as well as in the differential diagnosis on the basis of clinical findings alone (FIG. 3), but not very high in either list.

FIG. 4 illustrates the combined genome-phenome approach, including the clinical findings as in FIG. 3 and importing the genome variant table. The result of the combined genome-phenome approach is that Cohen syndrome, the definitive diagnosis, rises to the top of the differential diagnosis, with the probability shading indicating a very high probability for this diagnosis, and the finding of VPS13B biallelic mutations rises to have the highest pertinence of all pertinent positive findings (note that both gene findings such as VPS13B and clinical findings such as hypotonia have pertinence, as seen by background shading, but VPS13B has by far the highest pertinence of genes for which severe variants were found). By integrating both the genome information and the phenome information one can obtain much clearer information on diagnosis.

Example 2

Computing with Severity Scores that are Calculated as a Quantitative Result by Weighing Several Inputs In some embodiments, e.g., as described in Example 1, severity scores are imported as pre-calculated numbers. In alternative embodiments, severity scores are calculated as quantitative results by weighing one or more inputs from sequencing and bioinformatics analysis, for example the number of "reads" of a particular variant and the pathogenicity as assessed from modeling an amino acid substitution or truncation and using various widely available functional and conservation scores. By using a quantitative measure instead of using boolean "cut-offs" or "filters," the analysis may, in some instances, cast a wider net and consider variants that would be excluded by other approaches, and use the comparison to phenome information to highlight variants that may have been filtered out inappropriately by boolean filtering used in previous approaches, but then are elevated by their match to a particular phenotype. In one embodiment, such an analysis is computed using, e.g., a 43 column variant table instead of the 4 column variant table, with additional columns for zygosity in various other family members sequenced, variant frequency in the general population (overall, heterozygous and homozygous), chromosome location, type of variant (e.g. missense versus frameshift), various functional scores, various conservation scores, splice prediction scores, depth of read scores, read quality scores, scores based on whether a particular variant is known to cause disease, as well as other annotations used to denote and access information about particular genes (e.g. HGNC or OMIM listings).

Figure 5:
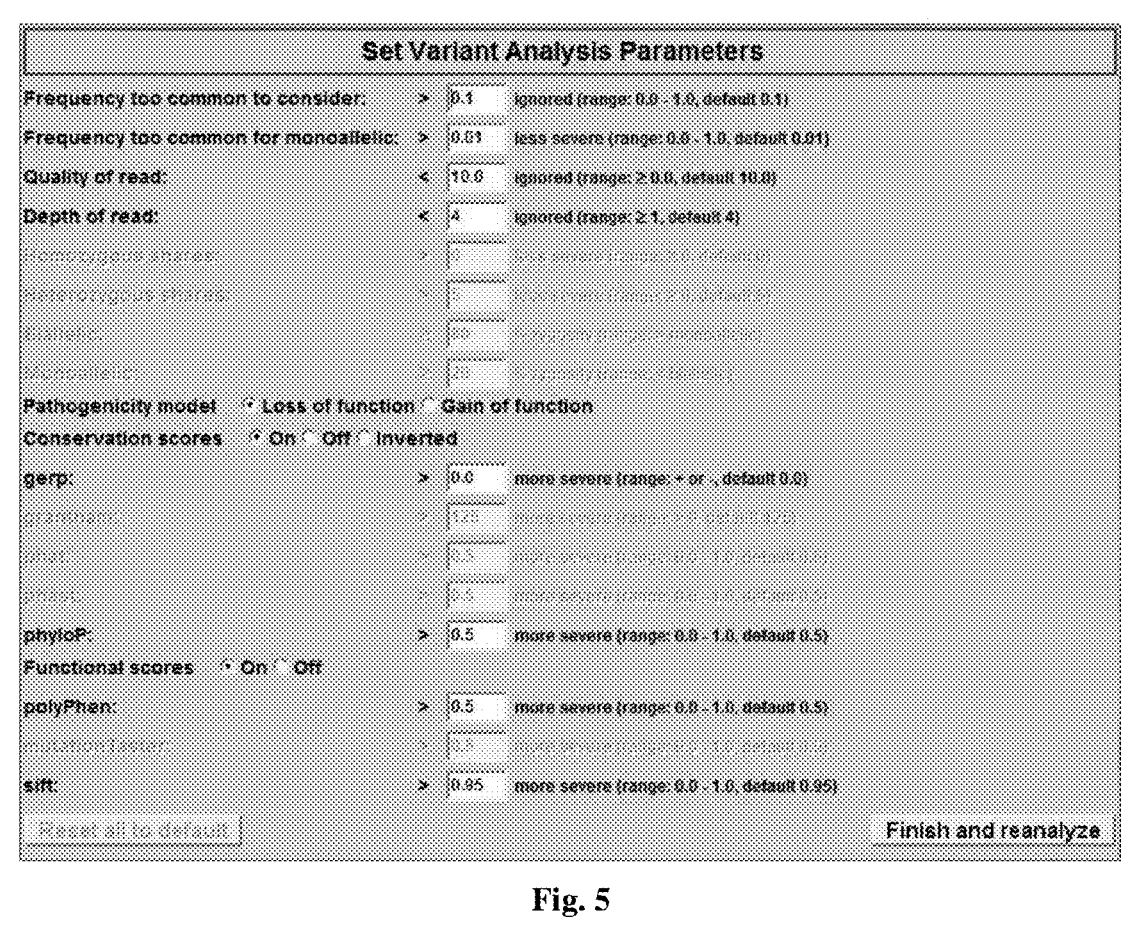

In some embodiments, the weightings of various criteria can be specified by the user, for example adjusting the tolerances for various annotation scores, including the frequency cutoff being so high as to cast doubt on monoallelic severity, as illustrated in FIG. 5 ("Frequency too common for monoallelic"). In some embodiments the pathogenicity model can be varied based on a loss of function pathogenicity model, as illustrated in FIG. 5, for example, giving a base severity score in a loss of function pathogenicity model of 4 to frameshift and 2 to missense, as opposed to 2 for frameshift and 4 for missense in a gain of function pathogenicity model. In addition, as illustrated in FIG. 5, conservation and functional scores can not only be used or ignored, but conservation scores can be inverted in the computation of severity scores, for example to look for a language gene in which the normal human form is likely to differ from those of related but non-human species. As a result of the systems and methods illustrated here, clicking the "Finish and reanalyze" button illustrated in FIG. 5 results in a full re-analysis of, e.g., a 43 column variant table with, e.g., ~35,000 variants in <2 seconds on a standard personal computer, making the ability to test such hypotheses such as gain of function pathogenicity (FIG. 5) or a parent being affected (not shown) practical in patient care.

Example 3

Computing with Zygosity

The methods, devices, and systems described herein include labeling each gene finding in the diagnostic software with known information about its zygosity, i.e. whether the genetic abnormality needed to produce disease is:

a) Autosomal monoallelic: a gene abnormality on only one of the two copies of a chromosome is needed to produce a disease termed an autosomal dominant disease;

b) Autosomal biallelic: a gene abnormality on both copies of a chromosome is needed to produce a disease termed an autosomal recessive disease;

c) X-linked: a gene abnormality is on the X-chromosome, of which males have only one copy, and are thus differently susceptible to such X-linked diseases;

d) Y-linked: a gene abnormality is on the Y-chromosome, of which only males have a copy, and only males can be affected by such Y-linked diseases; or e) Mitochondrial: a gene abnormality is on the mitochondrial DNA, of which males and females have only one copy.

Figure 6:
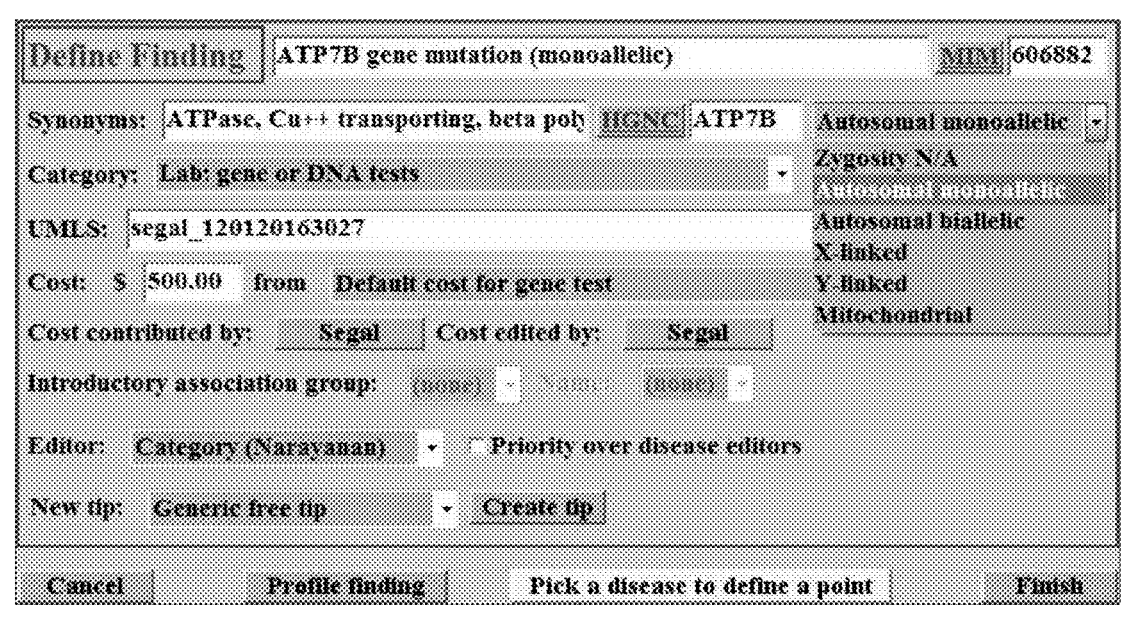

This labeling is illustrated in FIGS. 2 and 6, where the zygosity of the finding "ATP7B gene mutation (monoallelic)" is specified as "monoallelic." Such specification allows computing with the zygosity information from the variant table and assigning an ATP7B variant to the finding "ATP7B gene mutations (monoallelic)" versus "ATP7B gene mutation (biallelic)." This specification of zygosity is useful in the methods, devices, and systems described herein because findings with different zygosity may have different associations with disease. In the present Example, the monoallelic form of ATP7B mutation is associated with a carrier (heterozygous) state for Wilson disease that displays laboratory abnormalities but no clinical disease, while the biallelic form is associated with full Wilson disease. When the variant table is read into the software, default cutoff criteria, or in an alternative implementation illustrated in FIG. 5, cutoffs specified by the user, interpret 50% of DNA reads at one location being of the variant type as meeting criteria for the finding "ATP7B gene mutation (monoallelic)" but not "ATP7B gene mutations (biallelic)," resulting in "Wilson disease heterozygote" being listed high in the differential diagnosis, but full Wilson disease not being listed.

Similarly, X-linked diseases are recognized. Since this patient is female, the "ARX gene mutation (X-linked)" is scored from the 50% DNA level, and brings up the mild disease condition "ARX mental retardation, female heterozygotes," while if this had been a male, with only one X chromosome and thus ~100% DNA level had appeared in the variant table, the "ARX gene mutation (X-linked)" would have brought the more severe "ARX mental retardation" disease high in the differential diagnosis.

Using information in the variant table about chromosomal location, such an analysis can be done not only for genes with an identified human phenotype but for any gene. As illustrated in FIG. 7, even for unrecognized human phenotypes, knowledge of the chromosomal location as well as novelty and compound heterozygote analysis facilitates selection of possible inheritance models for genes, assigning severity scores, e.g., for autosomal monoallelic inheritance, autosomal biallelic inheritance, X-linked inheritance, and other inheritance models.

Example 4

Computing with Compound Heterozygotes

The data resulting from sequencing of many small fragments of DNA often reveals different variants in one gene, but leaves it unclear (without other types of testing) whether these abnormalities are in the same copy of the gene or the copy on the other copy of the chromosome. This information is clinically relevant for recessive diseases, in which one needs an abnormality on both copies of a gene to be affected by the disease. Accordingly, the methods, devices, and systems described herein look for the possibility of "compound heterozygotes," i.e., different abnormalities on each of the two copies of a gene. One approach is to keep track of the worst-case scenario in which the worst variants detected are on different copies of the chromosome. As an example, in the variant table in FIG. 1, after reading the first VPS13B variant of biallelic severity 2, there is insufficient evidence for the finding "VPS13B (COH1) gene mutations (biallelic)" since only one copy of the gene is affected (Proband %=50). After reading the second VPS13B variant of biallelic severity score 4, there is now a worst-case scenario of these variants being on opposite chromosomes, and therefore being a compound heterozygote with severity score 2 on one copy and severity score 4 on the other. This situation is judged to be severity 2 based on the need for both genes to be affected ("VPS13B (COH1) gene mutations (biallelic)") to produce the autosomal recessive disease "Cohen syndrome." When the next variant, with biallelic severity 3, is read in, the worst-case scenario is now severity score 4 on one gene copy and severity score 3 on the other, a situation with overall severity score 3. The result of this importing is shown in FIGS. 2 and 4, where the designation of "3c" is used for "VPS13B (COH1) gene mutations (biallelic)" to reflect the severity score of 3 based on compound heterozygosity. As a result of this compound heterozygosity for "VPS13B (COH1) gene mutations (biallelic)," Cohen syndrome is near the top of the differential diagnosis in FIG. 2 and after importing clinical information in addition to the genome variant table, it is at the top of the differential diagnosis in FIG. 4. The flagging as a compound heterozygote, e.g., using a "c" as shown in FIGS. 2 and 4, is useful to alert the clinician that the designation of this abnormality as biallelic is based on the worst-case scenario of two variants affecting different copies of the gene, a result that would need to be confirmed using other forms of gene testing, due to the limitations of the fragment sequencing approach. However, the automated genome-phenome analysis provides the clinical context for assessing the probability of Cohen syndrome, by adding additional pertinent positive and pertinent negative clinical and laboratory findings, and thus assists in the prioritization of such further testing for genes that are potentially compound heterozygotes.

Example 5

Putting Genome Information in the Context of Clinical Information and Identifying Pertinent Findings In whole genome analysis, many genes can be flagged as abnormal, so it is important to help the clinician focus on the genes most likely to be pertinent. This may be done, e.g., in two ways:

a) Identifying probable diseases: By combining both genome and clinical information together, one can get a read-out of the meaning of the genome in the context of the clinical information of interest. As an example, FIG. 8 shows the effect of using the same genome in the context of presence of "seizures" and the absence of fever-triggered episodes as the findings to explain (instead of the presence of "low weight" and "hypotonia" in FIG. 4). The different clinical information, combined with the same genome information as in previous figures, results in a differential diagnosis in which "Dravet syndrome" is the most likely diagnosis. In the more general situation, the clinical situation is described using several findings that are present ("pertinent positives") and several findings specified as absent ("pertinent negatives").

b) Identifying pertinent genes: By using a pertinence calculation, the clinician can be alerted to the clinical and laboratory results that are most important to evaluate. Pertinence may be determined, e.g., by assessing how different the differential diagnosis would be if that gene abnormality were not present. This may be achieved, e.g., as described above under the heading "Pertinence." The pertinence calculation may be used to rank and display gene abnormalities based on their pertinence and compare their pertinence to that of all other clinical and gene information known for the patient. As shown in FIG. 4, with the clinical findings of hypotonia and low weight, the VPS13B gene mutation is identified as having a high pertinence score, shown with shading, and high ranking in the list of the patient's findings. In contrast, in FIG. 8, with a different set of clinical findings that includes seizures, the SCN1A gene mutation is shown as having a high pertinence score, and a high ranking in the list of the patient's findings. As shown in FIG. 2, the user can change the severity score, e.g., using the drop down menu shown, to model the effect of a different gene severity score. Reducing the severity score for the SCN1A mutation from 3 (FIG. 8) to 1 (FIG. 9) results in the pertinence of the SCN1A mutation dropping (seen by less shading of the SCN1A finding button, and after a screen refresh (not shown), lower position in the list) and the ranking of SCN1A-related diseases such as Dravet syndrome becoming lower in the differential diagnosis and having less probability shading.

Figure 10:
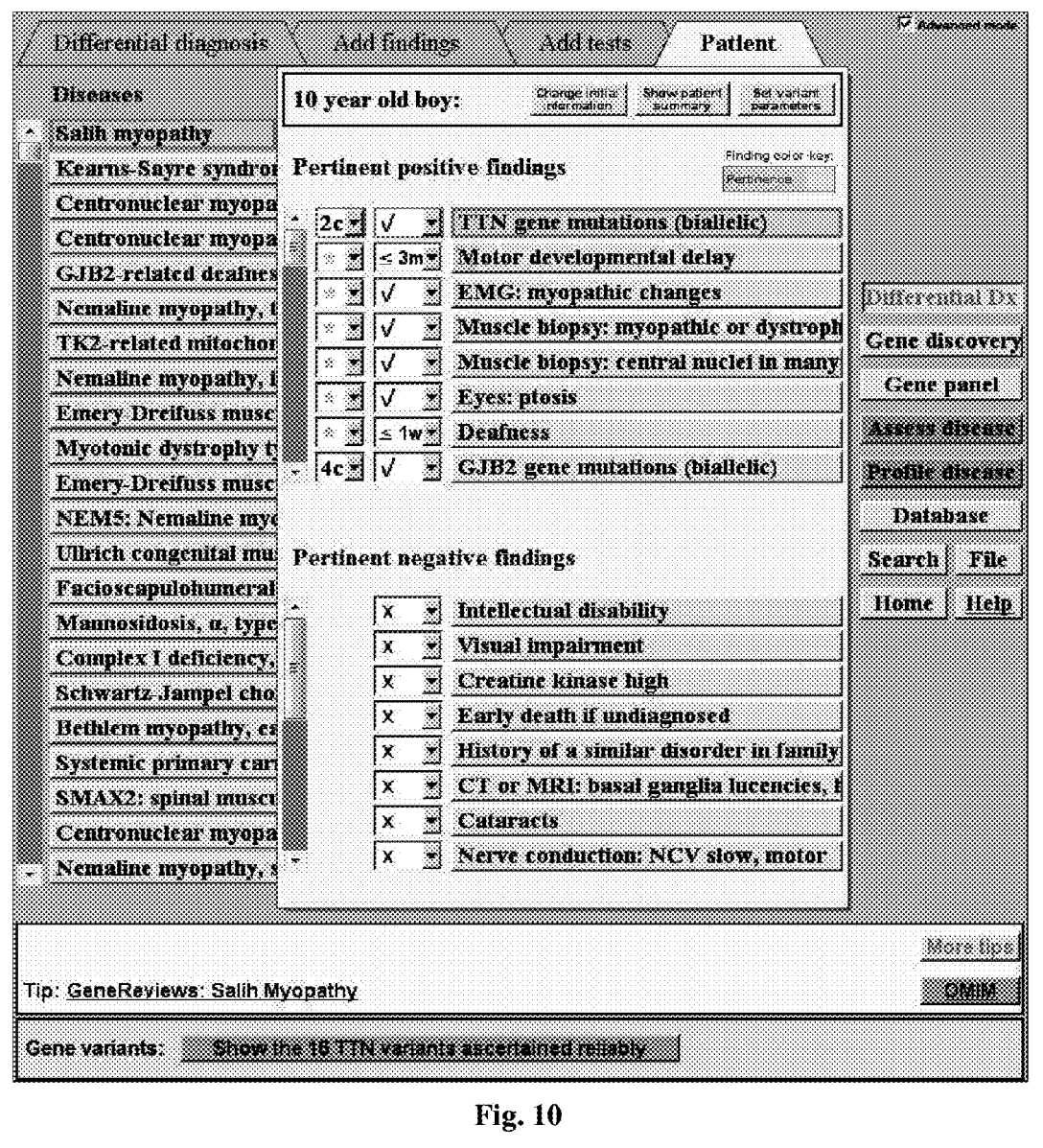

The pertinence calculation is very powerful since its application to genes can, for example, enable identifying two or more diagnoses that co-exist in a patient, and this can be done even when one of those diagnoses is not typical. FIG. 10 shows the results of importing a 43 column variant table with >32,000 variants from a proband, mother and father. The clinical symptoms included myopathy as well as central nuclei in muscle cells, a combination suggestive of centronuclear myopathy, for which several genes are known. However, the proband was also deaf, a finding associated with some myopathies, but not known to be associated with centronuclear myopathies. The automated genome-phenome analyzer found no significant severity for the known centronuclear myopathy genes, but assigned highest pertinence to variants in the TTN gene, despite a severity score of only 2. TTN mutations, central nuclei and myopathy are found in Salih myopathy, but since Salih myopathy had not been previously listed as a form of centronuclear myopathy, it would not have been on a "panel" list to check for centronuclear myopathy. Yet, the TTN mutations were #1 in gene pertinence, by such a wide margin that the TTN mutations were assigned almost all of the pertinence shading. The pertinence metric was also able to identify the cause of the deafness: GJB2 biallelic mutations, with severity 4, were ranked #2 in pertinence of genes among the >32,000 gene variants that were input. This identifies GJB2-related deafness as the cause for the patient's deafness, thereby determining that the clinical picture of centronuclear myopathy plus deafness was caused by the combination of atypical mutations in the TTN gene and typical mutations in the GJB2 gene.

Therefore, although one can analyze different hypotheses by choosing different clinical findings as illustrated in FIG. 4 versus FIG. 8, the power of the pertinence metric is such that one can analyze without the need for explicit hypotheses about which findings are caused by different genes, yet have 2 genes contributing to the clinical picture identified by the automated genome-phenome analyzer, as in FIG. 10, even though one had an atypical phenotype.

Example 6

Computing with Variant Information from Other Relatives

The imported variant table may contain information from only the individual being diagnosed or treated, or alternatively may further include variant information from other individuals, e.g., parents, siblings, or other family members. In some embodiments, information about variants present in family members may be used to eliminate certain compound heterozygote possibilities. For example, in the case of unaffected parents, if two genetic variants of the same gene are observed to be present in both the patient and the same parent, that would weigh against pathogenicity for the combination of the two genetic variants, and thus the combination of the two genetic variants could be eliminated from consideration in performing compound heterozygote analysis.

An illustrative example is shown in FIG. 11, in which variant information is available from the patient, mother and father. In this Example, both parents are unaffected; in other embodiments, one or both parents may be affected, and/or siblings or other family members, whether unaffected or affected, may also or alternatively be included in the analysis.

When compared to the patient-only variant table in FIG. 1, several differences are noted.

For the SCN1A variants, the first variant is designated as not novel because it is present in the mother as well, who is asymptomatic.

For the VPS13B variants, the first variant of 50% zygosity is not registered since the only VPS13B phenotypes are biallelic. The second VPS13B variant would be registered if only patient information were being considered, but in view of the available parental information, the second VPS13B variant is not registered. This is because both variants are from the mother, and therefore on the same chromosome and in the same copy of the gene in the patient. With addition of the third VPS13B variant, of paternal origin, it becomes clear that the patient has severity of 4 (the higher biallelic severity score for the two variants of maternal origin) and 2 (the biallelic severity score for the variant of paternal origin) on different copies of the VPS13B gene, thus getting a severity designation of 2, the lesser of the two values, as a compound heterozygote. With the addition of the fourth VPS13B variant, a novel variant not present in either parent and having biallelic severity of 3, the worst-case scenario is now 4 (maternal) and 3 (the higher biallelic severity score for the paternal and novel variants), thus designated as a compound heterozygote of severity 3 (the lesser of 4 and 3). However, it is equally possible that the situation is 4 (maternal, with novel) and 2 (paternal), and thus the labeling of "3c" serves to flag to the clinician the possibility that the severity of 3 is a worst-case scenario, and a severity of 2 might be the true situation, something that could be checked with other sequencing techniques that don't break genes into fragments of unknown parentage.

Figure 12:
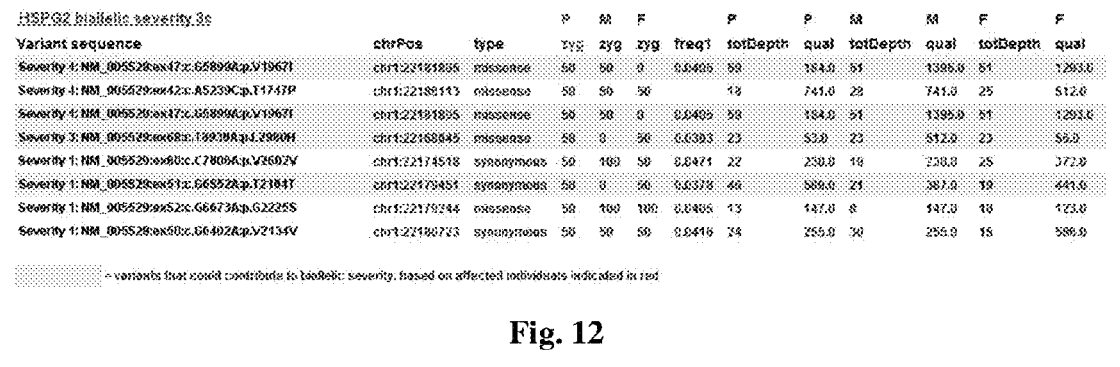

The variants underlying such computations are shown in FIG. 12, displayed by clicking a button such as the "Show the 16 TTN variants ascertained reliably" button seen at the bottom of FIG. 10. The display in FIG. 12 shows the variants for the HSPG2 gene in another patient that survives filtering based on variant read quality scores and variant frequency in the general population. The display illustrates how even though there are three variants assigned severity 4, one can't assign a biallelic severity score of 4 to this gene since all the variants with severity score 4 are present in 50% zygosity for the affected proband ("P zyg") and the unaffected mother ("M zyg"), and are thus all on the maternal copy of the chromosome, and thus cannot result in a compound heterozygote in the proband. Furthermore, as indicated by the chrPos column, two of these severity 4 variants are in fact alternate reads at the same chromosome position on the maternally-derived chromosome (and even if this were a novel mutation in the proband, a compound heterozygosity call would not be made based on calls at the same position). Also, one of the severity 4 variants is displayed un-shaded to indicate that it couldn't contribute to a compound heterozygote because there is no novel variant with which to pair the variant shared by proband and both parents to get biallelic severity that would not have been present in a parent as well. Two other variants are displayed un-shaded to indicate that the variant is not disease causing because it does not produce disease when present in 100% zygosity in a parent. Accordingly, a call of biallelic severity of severity 3 is made as a compound heterozygote, using one of the severity 4 variants derived from the unaffected mother and the severity 3 variant derived from the unaffected father.

Example 7

Procedure for Combined Novelty and Compound Heterozygosity Analysis

In some embodiments, the following procedure is used for combined novelty and compound heterozygosity analysis, in order to generate a refined determination of the severity score, for a "trio" consisting of an affected individual ("proband") and unaffected parents.

A. Consider only variants in which the proband zygosity is not wild type, the biallelic severity score is greater than zero, and neither unaffected parent is homozygous for the variant.

B. Examine all variants for a particular gene, keeping track of the following 5 values:
1. Both: Highest biallelic severity score for variants shared by proband and both parents
2. Mother: Highest biallelic severity score for variants shared by proband and mother, but not father
3. Father: Highest biallelic severity score for variants shared by proband and father, but not mother
4. Rank1Novel: Highest biallelic severity score for variants found in the proband but not present in either parent
5. Rank2Novel: Second highest biallelic severity score for variants found in the proband but not present in either parent C. Compute two models for compound heterozygotes by computing the First and Second most severe variants:
1. Using novel or uniparental variants only:
a. Assign FirstUni=Rank1Novel
b. Assign SecondUni=Rank2Novel
c. If Mother is greater than one or both of FirstUni and SecondUni, add it to the FirstUni/SecondUni list and drop the lowest
d. If Father is greater than one or both of FirstUni and SecondUni, add it to the FirstUni/SecondUni list and drop the lowest
2. Using novel or biparental variants only:
a. Assign FirstBi=Rank1Novel
b. Assign SecondBi=Rank2Novel
c. If Both is greater than one or both of FirstBi and SecondBi, add it to the FirstBi/SecondBi list and drop the lowest
3. Use the higher of SecondUni and SecondBi as the overall compound heterozygosity severity score.

The foregoing procedure may be modified as appropriate, e.g., to account for a fact pattern in which one or both parents are affected, and/or to include siblings or other family members, whether unaffected or affected, in the analysis.

Other Embodiments

All publications, patents, and patent applications mentioned in the above specification are hereby incorporated by reference in their entirety. In addition, U.S. Pat. No. 7,742,932 is hereby incorporated by reference in its entirety. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method comprising the steps of:
   (a) providing a plurality of patient findings for a patient being diagnosed in a physical computing device having a representation of a set of candidate diseases, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient, wherein for each of said one or more genetic variants, a severity score is provided in said plurality of patient findings or said computing device generates said severity score;
   (b) using said computing device to generate estimated probabilities of said candidate diseases using said plurality of patient findings and said severity scores for each of said one or more genetic variants;
   (c) generating the pertinence of said plurality of patient findings; and
   (d) outputting a candidate disease list capable of being displayed and ranked by highest said estimated probabilities and outputting a patient finding list capable of being displayed and ranked by pertinence.

2. The method of claim 1,
   wherein said computing device comprises a first set of quantities representing estimated probabilities of a plurality of patient findings in the general non-diseased population, and a second set of quantities representing estimated probabilities of a plurality of patient findings each assuming the presence of a specified candidate disease; and
   said method further comprises, in step (b), using said first set of quantities and second set of quantities to iteratively modify said initial parameters representing estimated probabilities of said candidate diseases using each of said plurality of patient findings to generate said estimated probabilities of said candidate diseases.

3. The method of claim 2, wherein said severity scores for each of said one or more genetic variants are used to modify one of said first set of quantities, said one of said first set of quantities representing an estimated probability of an abnormal gene with said genetic variant in the general non-diseased population.

4. The method of claim 3, wherein a higher severity score results in a lower said one of said first set of quantities representing an estimated probability of said abnormal gene with said genetic variant in the general non-diseased population.

5. The method of claim 3, wherein said genetic sequencing information associated with said patient comprises identification of a plurality of genetic variants each associated with the same gene, and wherein said genetic variant having the highest severity score among said genetic variants each associated with said gene is used to modify said one of said first set of quantities representing said estimated probability of said abnormal gene corresponding to said genetic variant absent information about the presence of a specified candidate disease.

6. The method of claim 1, wherein said severity score for each of said one or more genetic variants is generated by said computing device as a quantitative result from a plurality of inputs.

7. The method of claim 6, wherein said plurality of inputs comprise variant information from one or more parents, siblings, or other family members of said patient.

8. The method of claim 6, wherein said plurality of inputs comprises an input selected from the group consisting of: zygosity in one or more other family members sequenced, frequency of said genetic variant in the general population, chromosome location, type of said genetic variant, functional score, conservation score, splice prediction score, depth of read score, read quality score, and score based on whether said genetic variant is known to cause disease.

9. The method of claim 6, wherein said plurality of inputs comprises a pathogenicity model selected from the group consisting of a loss of function pathogenicity model and a gain of function pathogenicity model.

10. The method of claim 1, wherein said patient findings comprise, for at least one of said genetic variants identified, both a monoallelic severity score and a biallelic severity score.

11. The method of claim 10, wherein said monoallelic severity score is used when the corresponding genetic variant is considered to cause a monoallelic disease, and wherein said biallelic severity score is used when the corresponding genetic variant is considered to cause a biallelic disease.

12. The method of claim 11, wherein said monoallelic severity score is reduced, relative to said biallelic severity score, when the frequency of the corresponding genetic variant exceeds a threshold percentage of the population.

13. The method of claim 1, wherein said measure of zygosity for each said genetic variant is used to categorize said genetic variant as autosomal monoallelic, autosomal biallelic, X-linked monoallelic, X-linked biallelic, Y-linked, or mitochondrial.

14. The method of claim 13, wherein said genetic sequencing information associated with said patient comprises identification of two genetic variants each associated with the same gene, said two genetic variants each having monoallelic zygosity and said gene being associated with a recessive disease, and wherein said two genetic variants are collectively categorized as possibly having compound heterozygosity.

15. The method of claim 14, wherein said two genetic variants are collectively categorized as having a combined severity score corresponding to the lesser of the severity scores of said two genetic variants.

16. The method of claim 14, wherein said genetic sequencing information associated with said patient comprises identification of more than two genetic variants each associated with the same gene, said more than two genetic variants each having monoallelic zygosity and said gene being associated with a recessive disease, and wherein said more than two genetic variants are collectively categorized as possibly having compound heterozygosity and having a combined severity score corresponding to the lesser of the highest two severity scores of said more than two genetic variants.

17. The method of claim 15, wherein said patient findings further comprise, for at least one of said genetic variants identified, information about a parent, sibling, or other family member of said patient, said information comprising a measure of zygosity of said genetic variant in said family member.

18. The method of claim 17, wherein said information about said parent, sibling, or other family member of said patient is used to eliminate at least one compound heterozygote possibility, thereby resulting in a refined determination of said combined severity score.

19. The method of claim 13, wherein said genetic sequencing information associated with said patient comprises identification of two genetic variants each associated with the same gene, said two genetic variants each having monoallelic zygosity and said gene being associated with a recessive disease, wherein genetic sequencing information further comprises chromosomal location of said genetic variants, and wherein, if said chromosomal location is the same for each of said two genetic variants, said two genetic variants are not categorized as having compound heterozygosity.

20. The method of claim 13, wherein at least one of said genetic variants is of previously unidentified phenotype, wherein said genetic sequencing information comprises chromosomal location for said genetic variant, and wherein said measure of zygosity and said chromosomal location for said genetic variant are used to categorize said genetic variant as autosomal monoallelic, autosomal biallelic, X-linked monoallelic, X-linked biallelic, Y-linked, or mitochondrial.

21. The method of claim 1, wherein said patient findings further comprise information that is not obtained from genetic sequencing of genetic material from said patient, wherein said information that is not obtained from genetic sequencing of said genetic material from said patient comprises information about a laboratory test result, clinical result, or historical information associated with said patient.

22. The method of claim 1, wherein step (d) comprises transmitting said candidate disease list over the Internet or to a display device.

23. The method of claim 22, further comprising outputting to said display device said one or more candidate diseases having highest estimated probabilities in rank order.

24. The method of claim 1, wherein said method results in the diagnosis of said patient as having one of said candidate diseases having highest said estimated probabilities.

25. The method of claim 1, wherein said method results in the identification of one or more genes as having highest pertinence.

26. The method of claim 25, wherein said identification of said one or more genes as having highest pertinence results in the identification of one or more relationships between each said gene and a corresponding known disease or new variant similar to said known disease.

27. The method of claim 25, wherein said method results in the identification of two or more genes as having highest pertinence, wherein said identification of each of said two or more genes as having highest pertinence results in the identification of relationships between each said gene and a corresponding known disease or new variant similar to said known disease, and wherein said method results in the diagnosis of said patient as having each said corresponding known disease or new variant similar to said known disease.

28. The method of claim 1, wherein said physical computing device is accessed and operated over the Internet.

29. A computer readable medium having stored thereon executable instructions for directing a physical computing device to implement a method comprising the steps of:
   (a) providing a plurality of patient findings for a patient being diagnosed, in said physical computing device having a representation of a set of candidate diseases, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient;
   (b) generating a severity score for each of said one or more genetic variants;
   (c) generating estimated probabilities of said candidate diseases using said plurality of patient findings and said severity scores for each of said one or more genetic variants;
   (d) generating the pertinence of said plurality of patient findings; and
   (e) outputting a candidate disease list capable of being displayed ranked by highest said estimated probabilities and outputting a patient finding list capable of being displayed and ranked by pertinence.

30. A physical computing device having a representation of a set of candidate diseases and programmed with executable instructions for directing the device to implement a method comprising the steps of:
   (a) providing a plurality of patient findings for a patient being diagnosed, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient;
   (b) generating a severity score for each of said one or more genetic variants;
   (c) generating estimated probabilities of said candidate diseases using said plurality of patient findings and said severity scores for each of said one or more genetic variants;
   (d) generating the pertinence of said plurality of patient findings; and
   (e) outputting a candidate disease list capable of being displayed ranked by highest said estimated probabilities and outputting a patient finding list capable of being displayed and ranked by pertinence.

31. A method of diagnosing a patient in need thereof, said method comprising the steps of:
   (a) accessing a physical computing device comprising a representation of a set of candidate diseases, wherein:
      (i) said computing device receives a plurality of patient findings for said patient being diagnosed, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient, wherein for each of said one or more genetic variants, a severity score is provided in said plurality of patient findings or said computing device generates said severity score;

(ii) said computing device generates estimated probabilities of said candidate diseases using said plurality of patient findings and said severity scores for each of said one or more genetic variants; and (iii) said computing device generates the pertinence of said plurality of patient findings;

(b) receiving, from said physical computing device, a candidate disease list capable of being displayed ranked by highest said estimated probabilities and a patient finding list ranked by pertinence; and (c) diagnosing said patient as having one or more of said candidate diseases having highest said estimated probabilities.

32. A method of treating a patient in need thereof, said method comprising the steps of:

(a) accessing a physical computing device comprising a representation of a set of candidate diseases, wherein:

(i) said computing device receives a plurality of patient findings for a patient being diagnosed, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient, wherein for each of said one or more genetic variants, a severity score is provided in said plurality of patient findings or said computing device generates said severity score; and (ii) said computing device generates estimated probabilities of said candidate diseases using said plurality of patient findings and said severity scores for each of said one or more genetic variants; and (iii) said computing device generates the pertinence of said plurality of patient findings;

(b) receiving, from said physical computing device, a candidate disease list capable of being displayed ranked by highest said estimated probabilities and a patient finding list ranked by pertinence;

(c) diagnosing said patient as having one or more of said candidate diseases having highest said estimated probabilities; and (d) treating said patient for said one or more of said candidate diseases having highest said estimated probabilities as determined in step (c).

33. A method comprising providing, in a physical computing device, a representation of a set of candidate diseases, wherein:

(i) said computing device receives a plurality of patient findings for a patient being diagnosed, wherein each said patient finding in said plurality is representative of clinical or laboratory information gathered about said patient, and wherein said patient findings comprise genetic sequencing information associated with said patient comprising identification of one or more genetic variants, and for each of said one or more genetic variants, a measure of zygosity for said patient, wherein for each of said one or more genetic variants, a severity score is provided in said plurality of patient findings or said computing device generates said severity score;

(ii) said computing device generates estimated probabilities of said candidate diseases using said plurality of patient findings and said severity scores for each of said one or more genetic variants; and (iii) said computing device generates the pertinence of said plurality of patient findings;

(iv) said computing device outputs a candidate disease list capable of being displayed, ranked by highest said estimated probabilities and outputs a patient finding list capable of being displayed and ranked by pertinence.

34. A method comprising the steps of:

(a) receiving, in a physical computing device, a plurality of patient findings for a patient being diagnosed, wherein said patient findings comprise genetic sequencing information associated with said patient comprising identification of one or more genetic variants associated with a gene, and for each, a measure of zygosity for said patient, wherein for each of said one or more genetic variants, a severity score is provided in said plurality of patient findings or said computing device generates said severity score;

(b) using said measure of zygosity for each said genetic variant to categorize said one or more genetic variants, in said computing device, as autosomal monoallelic, autosomal biallelic, X-linked monoallelic, X-linked biallelic, Y-linked, or mitochondrial;

(c) using said computing device to identify two or more genetic variants each associated with the same gene, said two genetic variants each having monoallelic zygosity, wherein said two or more genetic variants are collectively categorized as possibly having compound heterozygosity;

(d) using said computing device to determine a combined severity score for said gene in step (c) corresponding to the lesser of the highest two severity scores of said two or more genetic variants in step (c);

(e) repeating steps (c) and (d) for each gene having two or more associated genetic variants; and (f) outputting a list comprising all or a subset of:

(i) each said gene having an associated genetic variant identified in step (a), and:

(ii) for each said gene having two or more genetic variants identified in step (c), said combined severity score associated with said gene determined in step (d); and for each said gene having only one genetic variant identified in step (a), said severity score associated with said genetic variant, wherein said list comprises genes with no previously described clinical findings, and wherein said list is capable of being displayed.

* * * * *

UNITED STATES PATENT AND TRADEMARK OFFICE
CERTIFICATE OF CORRECTION

| | | |
|---|---|---|
| PATENT NO. | : 9,524,373 B2 | Page 1 of 1 |
| APPLICATION NO. | : 13/781225 | |
| DATED | : December 20, 2016 | |
| INVENTOR(S) | : Segal | |

It is certified that error appears in the above-identified patent and that said Letters Patent is hereby corrected as shown below:

Column 1, Line 17 under STATEMENT REGARDING FEDERALLY SPONSORED RESEARCH, replace:

"This invention was made with government support under grant number 5R42HG006974 from the National Human Genome Research Institute. The government has certain rights to the invention."

with:

--This invention was made with government support under grant number 5R42HG006974 from the National Institutes of Health. The government has certain rights to the invention.--

Signed and Sealed this
Seventh Day of March, 2017

Michelle K. Lee
*Director of the United States Patent and Trademark Office*